US007132523B2

(12) United States Patent
Darrow et al.

(10) Patent No.: US 7,132,523 B2
(45) Date of Patent: Nov. 7, 2006

(54) HUMAN PRSS11-LIKE S2 SERINE PROTEASE AND USES THEREOF

(75) Inventors: Andrew Lawrence Darrow, Lansdale, PA (US); Jian-shen Qi, Branchburg, NJ (US); Cailin Chen, New Hope, PA (US); Patricia Andrade-Gordon, Doylestown, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 258 days.

(21) Appl. No.: 10/617,443

(22) Filed: Jul. 2, 2003

(65) Prior Publication Data

US 2005/0019777 A1 Jan. 27, 2005

Related U.S. Application Data

(63) Continuation-in-part of application No. 10/189,099, filed on Jul. 3, 2002, now abandoned.

(51) Int. Cl.
*C07H 21/04* (2006.01)
*C07H 15/00* (2006.01)
*C07H 1/19* (2006.01)
*C12N 15/63* (2006.01)
*C12N 1/20* (2006.01)

(52) U.S. Cl. .................. 536/23.2; 435/226; 435/252.3; 435/252.33; 435/254.2; 435/325; 435/348; 435/320.1

(58) Field of Classification Search ..................... None
See application file for complete search history.

(56) References Cited

OTHER PUBLICATIONS

Witkowski et al, Conversion of a beta-ketoacyl synthase to a malonyl decarboxylase by replacement of the active-site cysteine with glutamine. Biochemistry. Sep. 7, 1999;38(36):11643-11650.*
Wishart et al, A single mutation converts a novel phosphotyrosine binding domain into a dual-specificity phosphatase. J Biol Chem. Nov. 10, 1995;270(45):26782-26785.*
N_Geneseq_16Dec04 Database Accession No. AAV41533 from WO9824921 Jun. 11, 1998 Jalkanen et al. Alignment with residues 1-9 of SEQ ID No. 2.*
EST Database Accession No. BG548488 Apr. 4, 2001 Strausberg et al. Alignment with residues 1-1038 of SEQ ID No. 1.*
McDonagh et al., Production of caseinophosphopeptides (CPPs) from sodium caseinate using a range of commercial protease preparations. International Dairy Journal (1998), 8(1), 39-45.*

* cited by examiner

*Primary Examiner*—Sheridan Swope

(57) ABSTRACT

A novel human nucleic acid and polypeptide, termed PRSS11-L, are disclosed. PRSS11-L, which is observed in tissues throughout the body, can be used in methods of detection, gene therapy, and screening.

4 Claims, 5 Drawing Sheets

FIGURE 1 (1/2)

```
                                 1                                                   50
(SEQ ID NO: 9)  {CAA69226}       MQIPRAALLP LLLLLLAAPA SAQLSRAGRS APLAAGCPDR CEPARCPPQP
(SEQ ID NO: 2)  {PRSS11-Like}    ~~~~~~~~~~ ~~~~~~~~~~ ~~~~~~~~~~ ~~~~~~~~~~ ~~~~~~~~~~
(SEQ ID NO: 10) {AAB94569}       ~~~~~~~~~~ ~~~~~~~~~~ ~MAAPRAGRG AGWSLRAWRA LGGIRWGRRP
                Consensus        ---------- ---------- ---------- ---------- ----------

                                 51                                                 100
                {CAA69226}       EHCEGGRARD ACGCCEVCGA PEGAACGLQE GPCGEGLQCV VPFGVPASAT
                {PRSS11-Like}    ~~~~~~~~~~ ~~~~~~~~~~ ~~~~~~~~~~ ~~~~~~~~~~ ~~~~~~~~~~
                {AAB94569}       RLTPDLRALL TSGTSD...P RARVTYGTPS LWARLSVGVT EPRACLTSGT
                Consensus        ---------- ---------- ---------- ---------- ----------

                                 101                                                150
                {CAA69226}       VRRRAQAGLC VCASSEPVCG SDANTYANLC QLRAASRRSE RLHRPPVIVL
                {PRSS11-Like}    ~~~~~~~~~~ ~~~~~~~~~~ ~~~~~~~~~~ ~~~~~~~~~~ ~~~~~~~MHL
                {AAB94569}       PGPRAQLTAV TPDTRTREAS ENSGTRSRAW LAVALGAGGA VLLLLWGGGR
                Consensus        ---------- ---------- ---------- ---------- ----------

                                 151                                                200
                {CAA69226}       QRGACGQGQE D..PNSLRHK YNFIADVVEK IAPAVVHIEL FRKLPFSKRE
                {PRSS11-Like}    ALPA.SAGLH Q..LSSPRYK FNFIADVVEK IAPAVVHIEL FLRHPLFGRN
                {AAB94569}       GPPAVLAAVP SPPPASPRSQ YNFIADVVEK TAPAVVYIEI LDRHPFLGRE
                Consensus        ---A------ -----S-R-- -NFIADVVEK -APAVV-IE- ----P---R-

                                 201                     *                          250
                {CAA69226}       VPVASGSGFI VSEDGLIVTN AHVVTN.... ..KHRVKVEL KNGATYEAKI
                {PRSS11-Like}    VPLSSGSGFI MSEAGLIITN AHVVSSNSAA PGRQQLKVQL QNGDSYEATI
                {AAB94569}       VPISNGSGFV VAADGLIVTN AHVVAD.... ..RRRVRVRL LSGDTYEAVV
                Consensus        VP---GSGF- ----GLI-TN AHVV------ -------V-L --G--YEA--
```

FIGURE 1 (2/2)

```
               251    *                                                 300
{CAA69226}     KDVDEKADIA LIKIDHQGKL PVLLLGRSSE LRPGEFVVAI GSPFSLQNTV
{PRSS11-Like}  KDIDKKSDIA TIKIHPKKKL PVLLLGHSAD LRPGEFVVAI GSPFALQNTV
{AAB94569}     TAVDPVADIA TLRIQTKEPL PTLPLGRSAD VRQGEFVVAM GSPFALQNTI
Consensus      ---D---DIA ---I-----L P-L-LG-S-- -R-GEFVVA- GSPF-LQNT-

               301                                     *                350
{CAA69226}     TTGIVSTTQR GGKELGLRNS DMDYIQTDAI INYGNSGGPL VNLDGEVIGI
{PRSS11-Like}  TTGIVSTAQR EGRELGLRDS DMDYIQTDAI INYGNSGGPL VNLDGEVIGI
{AAB94569}     TSGIVSSAQR PARDLGLPQT NVEYIQTDAA IDFGNSGGPL VNLDGEVIGV
Consensus      T-GIVS--QR ----LGL--- ---YIQTDA- I--GNSGGPL VNLDGEVIG-

               351                                                      400
{CAA69226}     NTLKVTAGIS FAIPSDKIKK FLTESHDR.Q AKGKAITKKK YIGIRMMSLT
{PRSS11-Like}  NTLKVTAGIS FAIPSDRITR FLTEFQDK.Q IKD...WKKR FIGIRMRTIT
{AAB94569}     NTMKVTAGIS FAIPSDRLRE FLHRGEKKNS SSGISGSQRR YIGVMMLTLS
Consensus      NT-KVTAGIS FAIPSD---- FL-------- ---------- -IG--M----

               401                                                      450
{CAA69226}     SSKAKELKDR HRDFPDVISG AYIIEVIPDT PAEAGGLKEN DVIISINGQS
{PRSS11-Like}  PSLVDELKAS NPDFPEVSSG IYVQEVAPNS PSQRGGIQDG DIIVKVNGRP
{AAB94569}     PSILAELQLR EPSFPDVQHG VLIHKVILGS PAHRAGLRPG DVILAIGEQM
Consensus      -S---EL--- ---FP-V--G -----V---- P----G---- D-I-------

               451                                     489
{CAA69226}     VVSANDVSDV IKRESTLNMV VRRGNEDIMI TVIPEEIDP
{PRSS11-Like}  LVDSSELQEA VLTESPLLLE VRRGNDDLLF SIAPEVVM~
{AAB94569}     VQNAEDVYEA VRTQSQLAVQ IRRGRETLTL YVTPEVTE~
Consensus      ---------- ----S-L--- -RRG------ ---PE----
```

FIGURE 2 (1/1)

HtrA3 (BC034390) (SEQ ID NO: 11) x PRSS11-Like (SEQ ID NO: 2)

```
              .         .         .         .         .
101 CALQAASRRALQLSGTPVRQLQKGACP..LGLHQLSSPRYKFNFIADVVE 148
                                | |   |||||||||||||||||||
  1 ....................MHLALPASAGLHQLSSPRYKFNFIADVVE 29

              .         .         .         .         .
149 KIAPAVVHIELFLRHPLFGRNVPLSSGSGFIMSEAGLIITNAHVVSSNSA 198
    ||||||||||||||||||||||||||||||||||||||||||||||||||
 30 KIAPAVVHIELFLRHPLFGRNVPLSSGSGFIMSEAGLIITNAHVVSSNSA 79

              .         .         .         .         .
199 APGRQQLKVQLQNGDSYEATIKDIDKKSDIATIKIHPKKKLPVLLLGHSA 248
    ||||||||||||||||||||||||||||||||||||||||||||||||||
 80 APGRQQLKVQLQNGDSYEATIKDIDKKSDIATIKIHPKKKLPVLLLGHSA 129

              .         .         .         .         .
249 DLRPGEFVVAIGSPFALQNTVTTGIVSTAQREGRELGLRDSDMDYIQTDA 298
    ||||||||||||||||||||||||||||||||||||||||||||||||||
130 DLRPGEFVVAIGSPFALQNTVTTGIVSTAQREGRELGLRDSDMDYIQTDA 179

              .         .         .         .         .
299 IINYGNSGGPLVNLDGEVIGINTLKVTAGISFAIPSDRITRFLTEFQDKQ 348
    ||||||||||||||||||||||||||||||||||||||||||||||||||
180 IINYGNSGGPLVNLDGEVIGINTLKVTAGISFAIPSDRITRFLTEFQDKQ 229

              .         .         .         .         .
349 IKDWKKRFIGIRMRTITPSLVDELKASNPDFPEVSSGIYVQEVAPNSPSQ 398
    ||||||||||||||||||||||||||||||||||||||||||||||||||
230 IKDWKKRFIGIRMRTITPSLVDELKASNPDFPEVSSGIYVQEVAPNSPSQ 279

              .         .         .         .         .
399 RGGIQDGDIIVKVNGRPLVDSSELQEAVLTESPLLLEVRRGNDDLLFSIA 448
    ||||||||||||||||||||||||||||||||||||||||||||||||||
280 RGGIQDGDIIVKVNGRPLVDSSELQEAVLTESPLLLEVRRGNDDLLFSIA 329

449 PEVVM 453
    |||||
330 PEVVM 334
```

FIGURE 4

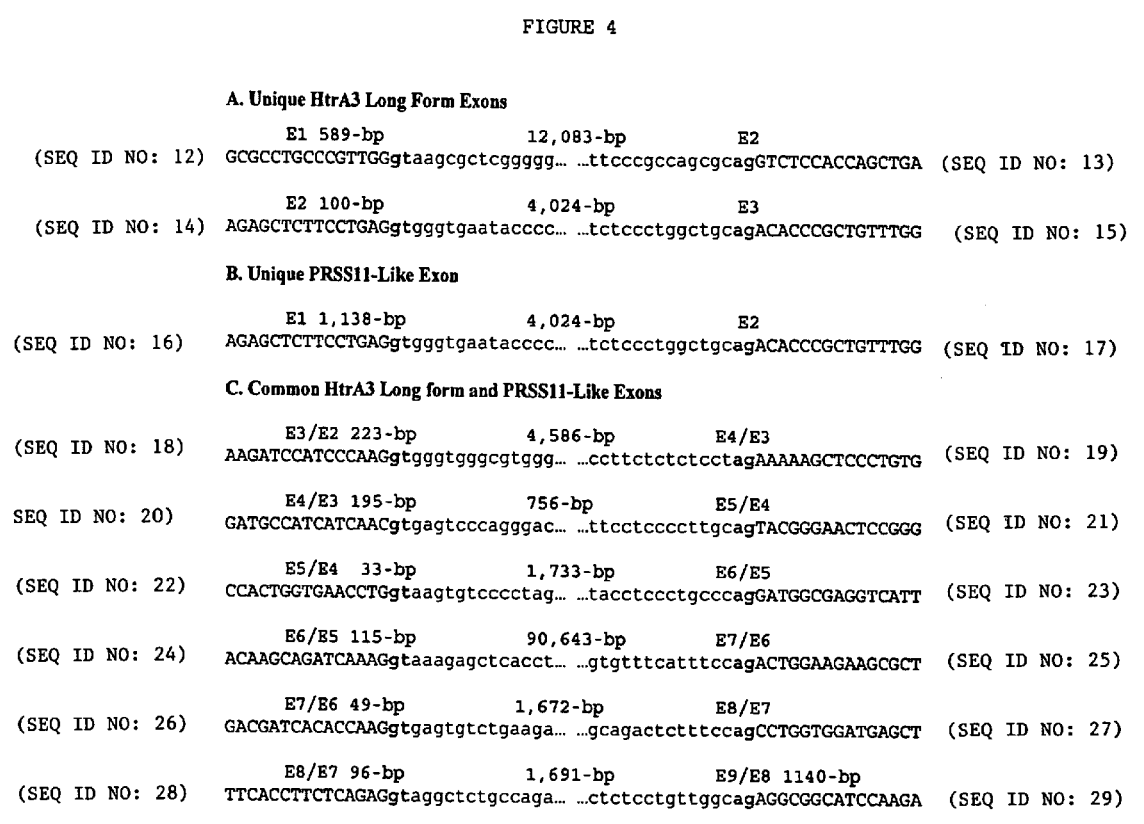

A. Unique HtrA3 Long Form Exons

E1 589-bp 12,083-bp E2

(SEQ ID NO: 12) GCGCCTGCCCGTTGGgtaagcgctcggggg... ...ttcccgccagcgcagGTCTCCACCAGCTGA (SEQ ID NO: 13)

E2 100-bp 4,024-bp E3

(SEQ ID NO: 14) AGAGCTCTTCCTGAGgtgggtgaataccccc... ...tctccctggctgcagACACCCGCTGTTTGG (SEQ ID NO: 15)

B. Unique PRSS11-Like Exon

E1 1,138-bp 4,024-bp E2

(SEQ ID NO: 16) AGAGCTCTTCCTGAGgtgggtgaataccccc... ...tctccctggctgcagACACCCGCTGTTTGG (SEQ ID NO: 17)

C. Common HtrA3 Long form and PRSS11-Like Exons

E3/E2 223-bp 4,586-bp E4/E3

(SEQ ID NO: 18) AAGATCCATCCCAAGgtgggtgggcgtggg... ...ccttctctctcctagAAAAAGCTCCCTGTG (SEQ ID NO: 19)

E4/E3 195-bp 756-bp E5/E4

SEQ ID NO: 20) GATGCCATCATCAACgtgagtcccagggac... ...ttcctccccttgcagTACGGGAACTCCGGG (SEQ ID NO: 21)

E5/E4 33-bp 1,733-bp E6/E5

(SEQ ID NO: 22) CCACTGGTGAACCTGgtaagtgtcccctag... ...tacctccctgcccagGATGGCGAGGTCATT (SEQ ID NO: 23)

E6/E5 115-bp 90,643-bp E7/E6

(SEQ ID NO: 24) ACAAGCAGATCAAAGgtaaagagctcacct... ...gtgtttcatttccagACTGGAAGAAGCGCT (SEQ ID NO: 25)

E7/E6 49-bp 1,672-bp E8/E7

(SEQ ID NO: 26) GACGATCACACCAAGgtgagtgtctgaaga... ...gcagactctttccagCCTGGTGGATGAGCT (SEQ ID NO: 27)

E8/E7 96-bp 1,691-bp E9/E8 1140-bp (SEQ ID NO: 28) TTCACCTTCTCAGAGgtaggctctgccaga... ...ctctcctgttggcagAGGCGGCATCCAAGA (SEQ ID NO: 29)

SEQUENCE LISTING

```
<160> NUMBER OF SEQ ID NOS: 8

<210> SEQ ID NO 1
<211> LENGTH: 3006
<212> TYPE: DNA
<213> ORGANISM: Homo sapiens

<400> SEQUENCE: 1

cagggactcg aagtttgcag tcctccacac tcagttccca cagatgtggt aggagggcat     60

attcagtccc atttttcaga tgaggagttg aggcccagag aacgtaagta atctgtctga    120

ggccacacag ctagaaagca gccaggccca gccgaacccc tggtgtgtgc agccccccagc    180

ccagttgctc attgcggggc tcgggagcca cgagcgaggc tgagcagcat gtgttccaga    240

tggtgggaac tggagagagc ccggcacagg cccgtgcagg gaaccccgag ggctgtaggc    300
```

-continued

```
cccgtgccac tgcatgcctc aggcctgtgg tcctggcagc cacagcccct actgctgacg    360
gcagcaggaa tctgagcccg ggaagggtcc agggaagttc gtgaaccatc tagcaagtcg    420
ggctggggtg tggccaagtt agacacagat gtagggccct gtggactcag aaattggcag    480
ctcttttggc ccagaggggc cacgctgtgt ccgggcctgg gtagctcaga agggtcacct    540
gggggtcttc cactacaccc ccgcctggac actgctgtag ccccagggct cggagggacc    600
agctggagcc catgaggaga gggccagttc tctcctgtaa gggtattgct gtagcatgag    660
ggaacagaca aggcccaggg ggactaaccc gagatccagc cccggcctca ctcccgtgtg    720
gctcacggca atatcctaac ctctctctga gcctcctgcc cagcctagca gggtccagtg    780
agggggggtga ggaagcccag cacgtggaag cctttttaac cattctcggg gtgagcgagc    840
cccttcccaa atgcctggtg tcactgcact gctgtgtggt agggggtccc caacgggctc    900
agtgtgggct gaggctggct ctgaactggg acaggggtct caggaagagc ctcctcctcc    960
tgcccactgg gcataggcct ctgggagctg gcagcatcgt gatctcactg atgcacctgg   1020
cccttcccgc cagcgcaggt ctccaccagc tgagcagccc gcgctacaag ttcaacttca   1080
ttgctgacgt ggtggagaag atcgcaccag ccgtggtcca catagagctc ttcctgagac   1140
acccgctgtt tggccgcaac gtgcccctgt ccagcggttc tggcttcatc atgtcagagg   1200
ccggcctgat catcaccaat gcccacgtgg tgtccagcaa cagtgctgcc ccgggcaggc   1260
agcagctcaa ggtgcagcta cagaatgggg actcctatga ggccaccatc aaagacatcg   1320
acaagaagtc ggacattgcc accatcaaga tccatcccaa gaaaaagctc cctgtgttgt   1380
tgctgggtca ctcggccgac ctgcggcctg gggagtttgt ggtggccatc ggcagtccct   1440
tcgccctaca gaacacagtg acaacgggca tcgtcagcac tgcccagcgg gagggcaggg   1500
agctgggcct ccgggactcc gacatggact acatccagac ggatgccatc atcaactacg   1560
ggaactccgg gggaccactg gtgaacctgg atggcgaggt cattggcatc aacacgctca   1620
aggtcacggc tggcatctcc tttgccatcc cctcagaccg catcacacgg ttcctcacag   1680
agttccaaga caagcagatc aaagactgga agaagcgctt catcggcata cggatgcgga   1740
cgatcacacc aagcctggtg gatgagctga aggccagcaa cccggacttc ccagaggtca   1800
gcagtggaat ttatgtgcaa gaggttgcgc cgaattcacc ttctcagaga ggcggcatcc   1860
aagatggtga catcatcgtc aaggtcaacg ggcgtcctct agtggactcg agtgagctgc   1920
aggaggccgt gctgaccgag tctcctctcc tactggaggt gcggcggggg aacgacgacc   1980
tcctcttcag catcgcacct gaggtggtca tgtgaggggc gcattcctcc agcgccaagc   2040
gtcagagcct gcagacaacg gagggcagcg cccccccgag atcaggacga aggaccaccg   2100
tcggtcctca gcagggcggc agcctcctcc tggctgtccg gggcagagcg gaggctgggc   2160
ttggccaggg gcccgaattt ccgcctgggg agtgttggat ccacatcccg gtgccgggga   2220
gggaagccca acatcccctt gtacagatga tcctgaaagt cacttccaag ttctccggat   2280
attcacaaaa ctgccttcca tggaggtccc ctcctctcct agcttcccgc ctctgcccct   2340
gtgaacaccc atctgcagta tcccctgctc ctgcccctcc tactgcaggt ctgggctgcc   2400
aagcttcttc ccccctgaca aacgcccacc tgacctgagg ccccagcttc cctctgccct   2460
aggacttacc aagctgtagg gccagggctg ctgcctgcca gcctggggtc cctggaggac   2520
aggtcacatc tgatcccttt ggggtgcggg ggtggggtcc agcccagagc aggcactgag   2580
tgaatgcccc ctggctgcgg agctgagccc cgccctgcca tgaggttttc ctccccaggc   2640
```

-continued

```
aggcaggagg ccgcggggag cacgtggaaa gttggctgct gcctggggaa gcttctcctc   2700

cccaaggcgg ccatggggca gcctgcagag gacagtggac gtggagctgc ggggtgtgag   2760

gactgagccg gcttcccctt cccacgcagc tctgggatgc agcagccgct cgcatggaag   2820

tgccgcccag aggcatgcag gctgctgggc accacccct catccaggga acgagtgtgt   2880

ctcaaggggc atttgtgagc tttgctgtaa atggattccc agtgttgctt gtactgtatg   2940

tttctctact gtatggaaaa taaagtttac aagcacacgg ttctcagcca aaaaaaaaaa   3000

aaaaaa                                                              3006


<210> SEQ ID NO 2
<211> LENGTH: 334
<212> TYPE: PRT
<213> ORGANISM: Homo sapiens

<400> SEQUENCE: 2

Met His Leu Ala Leu Pro Ala Ser Ala Gly Leu His Gln Leu Ser Ser
1               5                   10                  15

Pro Arg Tyr Lys Phe Asn Phe Ile Ala Asp Val Val Glu Lys Ile Ala
            20                  25                  30

Pro Ala Val Val His Ile Glu Leu Phe Leu Arg His Pro Leu Phe Gly
        35                  40                  45

Arg Asn Val Pro Leu Ser Ser Gly Ser Gly Phe Ile Met Ser Glu Ala
    50                  55                  60

Gly Leu Ile Ile Thr Asn Ala His Val Val Ser Ser Asn Ser Ala Ala
65                  70                  75                  80

Pro Gly Arg Gln Gln Leu Lys Val Gln Leu Gln Asn Gly Asp Ser Tyr
                85                  90                  95

Glu Ala Thr Ile Lys Asp Ile Asp Lys Lys Ser Asp Ile Ala Thr Ile
            100                 105                 110

Lys Ile His Pro Lys Lys Lys Leu Pro Val Leu Leu Leu Gly His Ser
        115                 120                 125

Ala Asp Leu Arg Pro Gly Glu Phe Val Val Ala Ile Gly Ser Pro Phe
    130                 135                 140

Ala Leu Gln Asn Thr Val Thr Thr Gly Ile Val Ser Thr Ala Gln Arg
145                 150                 155                 160

Glu Gly Arg Glu Leu Gly Leu Arg Asp Ser Asp Met Asp Tyr Ile Gln
                165                 170                 175

Thr Asp Ala Ile Ile Asn Tyr Gly Asn Ser Gly Gly Pro Leu Val Asn
            180                 185                 190

Leu Asp Gly Glu Val Ile Gly Ile Asn Thr Leu Lys Val Thr Ala Gly
        195                 200                 205

Ile Ser Phe Ala Ile Pro Ser Asp Arg Ile Thr Arg Phe Leu Thr Glu
    210                 215                 220

Phe Gln Asp Lys Gln Ile Lys Asp Trp Lys Lys Arg Phe Ile Gly Ile
225                 230                 235                 240

Arg Met Arg Thr Ile Thr Pro Ser Leu Val Asp Glu Leu Lys Ala Ser
                245                 250                 255

Asn Pro Asp Phe Pro Glu Val Ser Ser Gly Ile Tyr Val Gln Glu Val
            260                 265                 270

Ala Pro Asn Ser Pro Ser Gln Arg Gly Gly Ile Gln Asp Gly Asp Ile
        275                 280                 285
```

-continued

```
Ile Val Lys Val Asn Gly Arg Pro Leu Val Asp Ser Ser Glu Leu Gln
    290                 295                 300

Glu Ala Val Leu Thr Glu Ser Pro Leu Leu Leu Glu Val Arg Arg Gly
305                 310                 315                 320

Asn Asp Asp Leu Leu Phe Ser Ile Ala Pro Glu Val Val Met
                325                 330


<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: RACE primer

<400> SEQUENCE: 3

cagccgtgac cttgagcgtg ttg                                              23


<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: RACE primer

<400> SEQUENCE: 4

ggccgagtga cccagcaaca ac                                               22


<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 5

cgtgtctaga gccatgcacc tggcccttcc cgcc                                  34


<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 6

gcgctctaga catgaccacc tcaggtgcga                                       30


<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Internal
      primer

<400> SEQUENCE: 7

gcaagtcggg ctggggtgtg                                                  20


<210> SEQ ID NO 8
<211> LENGTH: 24
<212> TYPE: DNA
```

-continued

```
<213> ORGANISM: Artificial Sequence
<220> FEATURE:
<223> OTHER INFORMATION: Description of Artificial Sequence: Internal
      primer

<400> SEQUENCE: 8

cagggagctttttcttgggatgga                                              24
```

HUMAN PRSS11-LIKE S2 SERINE PROTEASE AND USES THEREOF

This application is a continuation-in-part of U.S. application Ser. No. 10/189,099 filed Jul. 3, 2002 (now abandoned), the entire contents of which are incorporated herein by reference.

FIELD OF THE INVENTION

The present invention relates to an S2 serine protease. In particular, the present invention relates to isolated nucleic acid molecules and polypeptides of a novel human S2 serine protease PRSS11-L and uses thereof.

BACKGROUND OF THE INVENTION

Two distinct members of the S2 serine protease subfamily have been previously identified in humans. One is protein L56/PRSS11 (Zumbrunn et al., (1996), *FEBS Lett.* 398: 187–192; Genbank Protein ID: CAA69226). The other is protein Omi/HtrA2 (Faccio et al., (2000), *J. Biol. Chem.* 275:2581–2588, Genbank Protein ID: AAB94569). These proteases share homologues with a bacterial HtrA (high-temperature requirement A) endoprotease, which acts as a chaperone at low temperatures and as a proteolytic enzyme that removes denatured or damaged substrates at elevated temperatures. The two members of human S2 serine proteases share extensive homology at their carboxy termini.

Human S2 serine proteases are believed to play important roles in cellular physiology. PRSS11 is upregulated in osteoarthritic cartilage and secreted. It was suggested that PRSS11 regulates the availability of IGFs by cleaving IGF-binding proteins. HtrA2 is upregulated during stress and appears to localize in the endoplasmic reticulum. It was shown that HtrA2 regulates apoptosis by interacting with the X chromosome-linked inhibitor of apoptosis (XIAP) (Suzuki et al., (2001), *Mol cell* 8:613–21).

SUMMARY OF THE INVENTION

The present invention relates to isolated nucleic acid molecules encoding a novel human S2 serine protease, herein referred to as PRSS11-L (PRSS11-Like), the polypeptides encoded by the isolated nucleic acid sequences, and the use of the nucleic acid molecules and polypeptides thereof.

BRIEF DESCRIPTION OF THE DRAWINGS

FIG. 1 depicts an alignment of the amino acid sequences of the PRSS11-L protein (SEQ ID NO: 2) and the two other S2 serine proteases, PRSS11 (SEQ ID NO: 9) (Genbank Protein ID: CAA69226) and Omi (SEQ ID NO: 10) (Genbank Protein ID: AAB94569). The alignment was performed using the Wisconsin GCG Gap Needleman and Wunsch algorithm. The active site residues of the catalytic triad are indicated above the sequences by asterisks (*).

FIG. 2 depicts an alignment of the amino acid sequences of the PRSS11-L protein (SEQ ID NO: 2) and HtrA3 (SEQ ID NO: 11) (Genbank Protein ID: AAH34390). The alignment was performed using the Wisconsin GCG Gap Needleman and Wunsch algorithm.

FIG. 4 shows the splice donor/acceptor sites for human HtrA3 and PRSS11-L transcripts on the HtrA3 gene. E stands for exon. Figure discloses SEQ ID NOS: 12–29, respectively, in order of appearance.

DETAILED DESCRIPTION

Definitions

Figure 3:
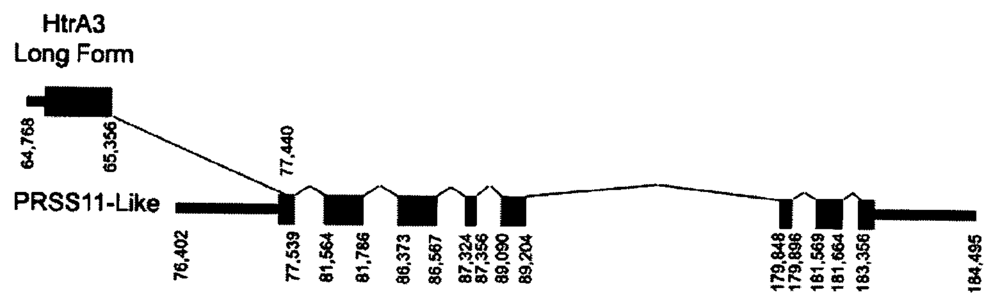
FIG. 3 is a schematic representation of the genomic structures of the PRSS11-L and HtrA3 long-form. The filled black boxes represent coding sequence exons while the filled bars represent the non-coding exons. The lines between exons represent introns. The numbers correspond to the nucleotide positions of the reverse complementary sequence to the BAC clone from human chromosome 4 (GenBank Accession No. AC113611).

As used herein, the term "family" refers to two or more proteins or nucleic acid molecules having a common structural domain and having the amino acid or nucleotide sequence identity defined herein. Family members can be from either the same or different species. For example, a family can comprises two or more proteins of human origin, or can comprise one or more proteins of human origin and one or more of non-human origin.

The term "protein superfamily" as used herein refers to proteins whose evolutionary relationship can not be entirely established or can be distant by accepted phylogenetic standards yet show similar three dimensional structures and/or display a unique consensus of critical amino acids.

"Nucleic acid molecule" used herein refers to a polynucleotide molecule. The term "polynucleotide(s)" generally refers to any polyribonucleotide or polydeoxribonucleotide, including unmodified RNA or DNA or modified RNA or DNA. A used herein, polynucleotide refers to, among others, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that can be single-stranded or, more typically, double-stranded, or triple-stranded, or a mixture of single- and double-stranded regions. DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides embraces short polynucleotides often referred to as oligonucleotide(s). For purposes of this disclosure, the term "nucleic acid" is also construed to include the complimentary sequence.

An "isolated" nucleic acid molecule is one which is substantially separated from nucleic acid molecules with differing nucleic acid sequences. Embodiments of the isolated nucleic acid molecule of the invention include cDNA as well as genomic DNA and RNA which are all preferably of human origin.

As used herein, the terms "gene" and "recombinant gene" refer to nucleic acid molecules comprising an open reading frame encoding a polypeptide.

The terms a "PRSS11-L gene", "gene for a PRSS11-L protease", and "gene for a PRSS11-L protein" as used herein, all refer to a DNA molecule that encodes a PRSS11-L protein. Examples of a "PRSS11-L gene" include DNA molecules characterized by a nucleotide sequence that is substantially similar to that from nucleotide 1011 to 2015 of SEQ ID NO: 1.

The term "regulatory region" or "regulatory sequence" is intended to include promoters, enhancers and other expression control elements (e.g., polyadenylation signals, and ribosome binding site (for bacterial expression) and/or, an operator). Such regulatory sequences are described and can be readily determined using a variety of methods known to those skilled in the art (see for example, in Goeddel, *Gene Expression Technology: Methods in Enzymology* 185, Academic Press, San Diego, Calif. (1990). Regulatory sequences include those that direct constitutive expression of a nucleotide sequence in many types of host cells and those that direct expression of the nucleotide sequence only in certain host cells (e.g., tissue-specific regulatory sequences).

As used herein, the term "allelic variant" refers to a nucleotide sequence which occurs at a given locus or to a polypeptide encoded by an allelic variant nucleotide sequence.

The term "polypeptide", as used herein, refers to the basic chemical structure of polypeptides that is well known and has been described in textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, can be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in the research literature, and are therefore well known to those of skill in the art. Among the known modifications which can be present in polypeptides of the present invention are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature.

Several particularly common modifications, such as glycosylation, lipid attachment, sulfation, gamma-carboxylation of glutamic acid residues, hydroxylation and ADP-ribosylation are described in many basic texts, including PROTEINS—STRUCTURE AND MOLECULAR PROPERTIES, 2nd Ed., T. E. Creighton, W. H. Freeman and Company, New York (1993). Many detailed reviews are also available on this subject, such as, for example, those provided by Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., (1990), *Meth. Enzymol.* 182, 626–646 and Rattan et al., "Protein Synthesis: Posttranslational Modifications and Aging", (1992) Ann. N.Y. Acad. Sci. 663, 48–62.

It will be appreciated, as is well known and as noted above, that polypeptides are not always entirely linear. For instance, polypeptides can be posttranslationly modified, including via natural processing or through human manipulation. Circular, branched and branched circular polypeptides can be synthesized by non-translation natural processes and by entirely synthetic methods, as well. Modifications can occur anywhere in a polypeptide, including the peptide backbone, the amino acid side-chains and the amino or carboxyl termini. In fact, blockage of the amino or carboxyl group or both in a polypeptide by a covalent modification, is common in naturally occurring and synthetic polypeptides and such modifications can be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus can be deleted. Accordingly, this invention contemplates the use of both the methionine-containing and the methionineless amino terminal variants of the protein of the invention.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as, for example, *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation, inter alia. Similar considerations apply to other modifications. It will be appreciated that the same type of modifications can be present in the same or varying degree at several sites in a given polypeptide. Also, a given polypeptide can contain many types of modifications. In general, as used herein, the term "polypeptide" encompasses all such modifications, particularly those that are present in polypeptides synthesized recombinantly by expressing a polynucleotide in a host cell.

The term "protein domain" as used herein refers to a region of a protein having a particular three-dimensional structure that has functional characteristics independent from the remainder of the protein. This structure can provide a particular activity to the protein. Exemplary activities include, without limitation, enzymatic activity, creation of a recognition motif for another molecule, or to provide necessary structural components for a protein to exist in a particular environment. Protein domains are usually evolutionarily conserved regions of proteins, both within a protein family and within protein superfamilies that perform similar functions.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest. Isolated biologically active polypeptide can have several different physical forms. The isolated polypeptide can exist as a full-length nascent or unprocessed polypeptide, or as partially processed polypeptides or combinations of processed polypeptides. The full-length nascent protease PRSS11-L polypeptide can be post-translationally modified by specific proteolytic cleavage events that results in the formation of fragments of the full length nascent polypeptide. A fragment, or physical association of fragments can have the full biological activity associated with protease PRSS11-L however, the degree of protease PRSS11-L activity can vary between individual protease PRSS11-L fragments and physically associated protease PRSS11-L polypeptide fragments. The terms "a PRSS11-L polypeptide", "a PRSS11-L protease", and "a PRSS11-L protein" as used herein, all refer to a novel member of the S2 serine protease characterized by an amino acid sequence that is substantially similar to that shown in SEQ ID NO:2, and comprises an amino acid sequence having at least a 90% identity to amino acid 1 to 9 of SEQ ID NO:2. The term "substantially similar" as used herein, includes identical sequences, as well as deletions, substitutions or additions to a polynucleotide or polypeptide sequence that maintain any biologically active portion thereof of the protein product and possess any of the conserved motifs.

"An activity", "a biological activity", or "a functional activity" of a polypeptide or nucleic acid of the invention refers to an activity exerted by a polypeptide or nucleic acid molecule of the invention as determined in vivo, or in vitro, according to standard techniques. Such activities can be a direct activity, such as an association with or an enzymatic activity on a second protein, or an indirect activity, such as a cellular signaling activity mediated by interaction of the protein with a second protein. The biological activities of PRSS11-L include, but not limited to, (1) the ability to act as a proteolytic enzyme cleaving either itself (e.g., autocatalysis), or other substrates; (2) the ability to bind to an inhibitor or enhancer of proteolytic enzyme activity, e.g., an inhibitor of a serine protease, or some other proteins; (3) the ability to act as a chaperone protein, e.g., to renature misfolded proteins and help to restore their function; (4) the ability to perform one or more of the described functions of the S2 serine protease, such as that of human HtrA (Hu et al., (1998), *J. Biol. Chem.* 273(51):34406–34412, Suzuki et al., (2001), *Mol Cell* 8:613–21).

"Sequence identity or similarity", as known in the art, is the relationship between two or more polypeptide sequences or two or more polynucleotide sequences, as determined by comparing the sequences. In the art, identity also means the degree of sequence relatedness between polypeptide or polynucleotide sequences, as the case can be, as determined by the match between strings of such sequences. To determine the percent identity or similarity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same or similar amino acid residue or nucleotide as the corresponding position in the second sequence, then the molecules are identical or similar at that position. The percent identity or similarity between the two sequences is a function of the number of identical or similar positions shared by the sequences (i.e., % identity=# of identical positions/total # of positions (e.g., overlapping positions)×100). In one embodiment, the two sequences are the same length.

Both identity and similarity can be readily calculated. Methods commonly employed to determine identity or similarity between sequences include, but are not limited to those disclosed in Carillo et al, (1988), *SIAM J. Applied Math.* 48, 1073. Preferred methods to determine identity are designed to give the largest match between the sequences tested. Methods to determine identity and similarity are codified in computer programs.

A preferred, non-limiting example of a mathematical algorithm utilized for the comparison of two sequences is the algorithm of Karlin et al., (1990), Proc. Natl. Acad. Sci. USA 87:2264–2268, modified as in Karlin et al., (1993), Proc. Natl. Acad. Sci. USA 90:5873–5877. Such an algorithm is incorporated into the NBLAST and XBLAST programs of Altschul et al., (1990), J. Mol. Biol 215: 403–410. To obtain gapped alignments for comparison purposes, Gapped BLAST can be utilized as described in Altschul et al., (1997), Nucleic Acids Res. 25:3389–3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. Additionally, there is the FASTA method (Atschul et al., (1990), J. Molec. Biol. 215, 403), which can be used.

Another preferred, non-limiting example of a mathematical algorithm useful for the comparison of sequences is the algorithm of Myers et al, (1988), *CABIOS* 4:11–17. Such an algorithm is incorporated into the ALIGN program (version 2.0) which is part of the GCG sequence alignment software package (Devereux et al., (1984), *Nucleic Acids Research* 12(1), 387).

The percent identity between two sequences can be determined using techniques similar to those described above, with or without allowing gaps. In calculating percent identity, only exact matches are counted.

As used herein, the term "vector" refers to a nucleic acid molecule capable of transporting another nucleic acid to which it has been linked. One type of vector is a "plasmid", which refers to a circular double stranded DNA loop into which additional DNA segments can be inserted. Another type of vector is a viral vector, wherein additional DNA segments can be inserted. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover expression vectors are capable of directing the expression of genes to which they are operably linked. In general, vectors of utility in recombinant DNA techniques are often in the form of plasmids. However, the invention is intended to include other types of vectors, such as viral vectors (e.g., replication defective retroviruses, adenoviruses and adeno-associated viruses), which serve equivalent functions.

The term "linker region" or "linker domain" or similar such descriptive terms as used herein refers to one or more polynucleotide or polypeptide sequences that are used in the construction of a cloning vector or fusion protein. The function of a linker region can include introduction of cloning sites into the nucleotide sequence, introduction of a flexible component or space-creating region between two protein domains, or creation of an affinity tag to facilitate a specific molecule interaction. A linker region can be introduced into a fusion protein, if desired, during polypeptide or nucleotide sequence construction.

The term "cloning site" or "polycloning site" as used herein refers to a region of the nucleotide sequence that has one or more available restriction endonuclease consensus cleavage sequences. These nucleotide sequences can be used for a variety of purposes including, but not limited to, introduction of these sequences into DNA vectors to create novel fusion proteins, or to introduce specific site-directed mutations. It is well known by those of ordinary skill in the art that cloning sites can be engineered at a desired location by silent mutation, conserved mutation, or introduction of a linker region that contains desired restriction endonuclease recognition sequences. It is also well known by those of ordinary skill in the art that the precise location of a cloning site can be engineered into any location in a nucleotide sequence.

The term "tag" as used herein refers to an amino acid sequence or a nucleotide sequence that encodes an amino acid sequence that facilitates isolation, purification or detection of a protein containing the tag. A wide variety of such tags are known to those skilled in the art and are suitable for use in the present invention. Suitable tags include, but are not limited to, HA peptide, polyhistidine peptides, biotin/avidin, and a variety of antibody epitope binding sites.

As used herein, the term "host cell" refers to a cell that contains a DNA molecule of the invention either on a vector or integrated into a cell chromosome.

As used herein, a "recombinant host cell" is a cell which has been transformed or transfected, or is capable of transformation or transfection by an exogenous DNA sequence. As used herein, a cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA. Recombinant host cells may be prokaryotic or eukaryotic, including but not limited to bacteria such as *E. coli*, fungal cells such as yeast, mammalian cells including but not limited to cell lines of human, bovine, porcine, monkey and rodent origin, and insect cells including but not limited to *Drosophila* and silkworm derived cell lines. It is further understood that the term "recombinant host cell" refers not only to the particular subject cell but also to the progeny or potential progeny of such a cell. Because certain modifications can occur in succeeding generations due to either mutation or environmental influences, such progeny may not, in fact, be identical to the parent cell, but are still included within the scope of the term as used herein.

As used herein, a "clone" is a population of cells derived from a single cell or common ancestor by mitosis. A "cell line" is a clone of a primary cell that is capable of stable growth in vitro for many generations.

As used herein, the term "a biological sample" can be tissues, cells and biological fluids isolated from a subject, as well as tissues, cells and fluids present within a subject. In one embodiment, the biological sample contains protein molecules from the subject. The protein molecules may or may not remain their native biological activities. In another embodiment, the biological sample contains nuclei acid including genomic DNA, and/or mRNA molecules from the test subject or from the subject. In yet another embodiment, the biological sample contains both proteins and nucleic acid molecules.

As used herein, the term "a disorder related to PRSS11-L" shall include a disorder or disease associated with overactivity or insufficient activity of PRSS11-L, and conditions that accompany this disorder or disease.

The term "overactivity of PRSS11-L" refers to either 1) PRSS11-L expression in cells which normally do not express PRSS11-L; 2) increased PRSS11-L expression; or 3) mutations leading to constitutive activation of one or more PRSS11-L biological activities.

The term "insufficient activity of PRSS11-L" refers to either 1) the absence of PRSS11-L expression in cells which normally express PRSS11-L; 2) decreased PRSS11-L expression; or 3) mutations leading to constitutive inactivation of one or more PRSS11-L biological activities.

The term "subject" as used herein, refers to an animal, preferably a mammal, most preferably a human, who has been the object of treatment, observation or experiment.

Unless defined otherwise, all technical and scientific terms used herein have the same meaning as is commonly understood by one of skill in the art.

Protease PRSS11-Like Nucleic Acid Molecules

One aspect of the invention pertains to isolated nucleic acid molecules that encode a PRSS11-Like protease or a biologically active portion thereof, as well as nucleic acid molecules of at least 12 sequential nucleotides in length for use as hybridization probes or PCR primers, to identify or amplify nucleic acid molecules encoding a PRSS11-L polypeptide of the invention.

Isolated Nucleic Acid Molecule of the Invention

In one embodiment, the invention provides an isolated nucleic acid molecule capable of encoding a S2 serine protease, comprising a nucleotide sequence encoding a polypeptide which has at least a 90% sequence identity to amino acids 1 through 9 of SEQ ID NO: 2, or a complement thereof. A nucleic acid molecule which is a complement of a given nucleotide sequence is one which is sufficiently complementary to the given nucleotide sequence that it can hybridize to the given nucleotide sequence thereby forming a stable duplex under high stringency (i.e., stringent hybridization conditions).

Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

In another embodiment, the invention provides an isolated nucleic acid molecule comprising at least 12 sequential nucleotides of SEQ ID NO:1 from nucleotide 1 to 1038, or the complement thereof. Nucleic acid probes that hybridize to this region under stringent hybridization condition are highly desirable for identifying and/or cloning homologues of PRSS11-L in other cell types, e.g., from other tissues, as well as homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO: 1, nucleotides 1 to 1038.

In yet another embodiment, the invention provides an isolated nucleic acid molecule having at least 70% sequence identity to SEQ ID NO:1, nucleotides 1 to 1038, or the complement thereof, such nucleic acid molecules are potentially capable of regulating gene expression of PRSS11-L in gene therapy.

In a preferred embodiment, the invention provides an isolated nucleic acid molecule comprising the nucleotide sequence of SEQ ID NO: 1, or a complement thereof.

In another preferred embodiment, the invention provides an isolated nucleic acid molecule comprising a nucleotide sequence encoding a polypeptide of SEQ ID NO: 2, or a complement thereof. For example, the invention provides an isolated nucleic acid molecule that comprises a nucleic acid molecule which is a degenerate variant of PRSS11-L DNA as set forth in SEQ ID NO: 1, or a complement thereof. It is known that more than one genetic codon can be used to encode a particular amino acid, and therefore, the amino acid sequence of PRSS11-L protein SEQ ID NO: 2 can be encoded by any of a set of similar DNA molecules. Only one member of the set will be identical to PRSS11-L DNA as set forth in SEQ ID NO: 1; however all variants hereinafter referred to as degenerate variants are contemplated within the scope of this invention. Herein, a nucleic acid molecule bearing one or more alternative codons which encodes a polypeptide with amino acid sequence set forth as SEQ ID NO: 2, is defined as a degenerate variant of PRSS11-L DNA as set forth in SEQ ID NO: 1.

Particularly preferred in this regard are natural allelic variants of PRSS11-L nucleic acid molecules. DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. Such natural allelic variations can typically result in 1–5% variance in the nucleotide sequence of a given gene. Alternative alleles can be identified by sequencing the gene of interest in a number of different individuals, or by using hybridization probes to identify the same genetic locus in a variety of individuals.

Further particularly preferred in this regard are nucleic acid molecules having any and all such nucleotide variations that are not known to occur naturally and which encode polypeptides having properties that are different than, but still maintain the functional activity of, the naturally occurring PRSS11-L protein. In addition to a naturally occurring variant such as a naturally occurring allelic variant, a variant of the polynucleotide or polypeptide can also be a variant that is not known to occur naturally. DNA sequences can be altered manually so as to code for a peptide having properties that are different from those of the naturally occurring peptide. Methods of altering the DNA sequences include, but are not limited to, site directed mutagenesis, chimeric substitution, and gene fusions. Site-directed mutagenesis is used to change one or more DNA residue and can result in one or more silent mutations, conservative mutations, or nonconservative mutations. Chimeric genes are prepared by swapping domains of similar or different genes to replace similar domains in the protease PRSS11-L gene. Similarly, fusion genes can be prepared that add domains to the protease PRSS11-L gene, such as an affinity tag to facilitate identification and isolation of the gene and protein, or a signal sequence to make PRSS11-L a secreted protein.

The variants of the PRSS11-L nucleic acid molecule of the invention are capable of hybridizing to SEQ ID NO: 1 under high stringent hybridization condition.

Isolation of PRSS11-L Nucleic Acid Molecules

The present invention provides methods of isolating PRSS11-L nucleic acid molecules. Because PRSS11-L is widely expressed in several tissues (Example 3), many cells and cell lines other than prostate cells can also be suitable as a source for the isolation of PRSS11-L cDNA. Selection of suitable cells as a cDNA source can be done by screening for the presence of PRSS11-L transcripts in cell extracts or in whole cell assays by Northern analysis using primers that hybridize specifically to PRSS11-L transcript. Cells that possess PRSS11-L transcript, preferably high levels of PRSS11-L transcript, are suitable for the isolation of PRSS11-L cDNA or mRNA.

Any of a variety of procedures known in the art can be used to isolate a nucleic acid molecule encoding a PRSS11-L protein. For example, using cDNA or genomic DNA libraries, or total mRNA from the suitable cells identified above as a template and appropriate oligonucleotide as primers, a nucleic acid molecule of the invention can be amplified according to standard PCR amplification techniques. The nucleic acid so amplified from PCR can be cloned into an appropriate vector and characterized by DNA sequence analysis. The ordinarily skilled artisan will appreciate that oligonucleotides comprising at least 12 contiguous nucleotides of SEQ ID NO:1 are particularly useful as primers. The primers can be prepared by standard synthetic techniques, e.g., using an automated DNA synthesizer. Particularly preferred primers are those that can be used to detect PRSS11-L gene but do not bind to other known S2 serine protease genes, such as pPRSS11 or HtrA2.

Another method to isolate PRSS11-L nucleic acid molecules is to probe a genomic or cDNA library, or total mRNA with one or more natural or artificially designed probe using procedures recognized by those familiar with the art. See, e.g., "Current Protocols in Molecular Biology", Ausubel et al.(eds.) Greene Publishing Association and John Wiley Interscience, New York, 1989,1992. The ordinarily skilled artisan will appreciate that SEQ ID NO: 1 or fragments thereof comprising at least 12 contiguous nucleotides are particularly useful probes. Preferred probes will have at least 30 bases. Particularly preferred probes will have 50 or less bases. It is also appreciated that such probes can be and are preferably labeled with an analytically detectable reagent to facilitate identification of the probe. Useful reagents include, but are not limited to, radioisotopes, fluorescent dyes or enzymes capable of catalyzing the formation of a detectable product. The probes enable the ordinarily skilled artisan to isolate complementary copies of genomic DNA, cDNA or RNA polynucleotides encoding PRSS11-L proteins from human, mammalian or other animal sources or to screen such sources for related sequences, e.g., additional members of the family, type and/or subtype, including transcriptional regulatory and control elements as well as other stability, processing, translation and tissue specificity-determining regions from 5' and/or 3' regions relative to the coding sequences disclosed herein, all without undue experimentation.

Another method to prepare nucleic acid molecules corresponding to all or a portion of a nucleic acid molecule of the invention is by standard synthetic techniques, e.g., using an automated DNA synthesizer.

Another method to isolate PRSS11-L nucleic acid molecules is by using a reverse genetics method. In this example, the protease PRSS11-L is purified and the partial amino acid sequence is determined by automated amino acid sequenators. It is not necessary to determine the entire length of the amino acid sequence, but the linear sequence of two regions of at least about 4 to 8 amino acids from the protein is necessary for the production of primers for PCR amplification of a partial PRSS11-L DNA fragment. Once suitable amino acid sequences have been identified, the DNA sequences capable of encoding them can either be synthesized by standard synthetic techniques, e.g., using an automated DNA synthesizer, or by degenerate PCR according to established PCR amplification techniques using cDNA or genomic DNA libraries, or total mRNA as a template and to produce 15 to 30 degenerate oligonucleotides deduced from the amino acid sequence as primers. Because more than one genetic codon can be used to encode a particular amino acid, the amino acid sequence can be encoded by any of a set of similar DNA oligonucleotides. Thus, the frequency of codon usage in a particular host is taken into account in designing the degenerate PCR primers based on the known amino acid sequence. Often, each primer contains a pool of oligonucleotides to encourage specific hybridization to the template DNA. Although maximally only one member of the pool will be identical to the protease PRSS11-L sequence and will be capable of hybridizing to protease PRSS11-L DNA, slightly mismatched primers are also able to hybridize to the protease PRSS11-L DNA under moderately stringent hybridization conditions to initiate a PCR amplification reaction.

Preparation of cDNA libraries from the identified source cell can also be performed by standard techniques well known in the art. Well known cDNA library construction techniques can be found for example, in Maniatis et al., Molecular Cloning: A Laboratory Manual, Second Edition (Cold Spring Harbor Laboratory, Cold Spring Harbor, N.Y., 1989).

Isolation of total mRNA from the identified source cell can be performed by standard techniques well known in the art. Well known techniques of total mRNA isolation can be found for example, in Maniatis et al., supra.

Construction of genomic DNA libraries can be performed by standard techniques well known in the art. Well known genomic DNA library construction techniques can be found in Maniatis et al., supra.

Recombinant Expression Vectors and Host Cells

Another aspect of the invention pertains to vectors, preferably expression vectors, containing a nucleic acid of the present invention.

Recombinant Expression Vectors

The recombinant expression vectors of the invention comprise a nucleic acid of the invention in a form suitable for expression of the nucleic acid in a host cell. This means that the recombinant expression vectors include one or more regulatory sequences. The sequences can be selected on the basis of the host cells to be used for expression. The regulatory sequences are operably linked to the nucleic acid sequence to be expressed. Within a recombinant expression vector, “operably linked” is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., *E. coli*) or eukaryotic cells (e.g., insect cells (using baculovirus expression vectors), yeast cells or mammalian cells). Suitable host cells are known to those skilled in the art. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve four purposes: 1) to increase expression of recombinant protein; 2) to increase the solubility of the recombinant protein; 3) to aid in the purification of the recombinant protein by acting as a ligand in affinity purification; and/or 4) to facilitate detection of the recombinant protein by serving as a marker. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith et al., (1988), Gene 67:31–40), pMAL (New England Biolabs, Beverly, Mass.), pRIT5 (Pharmacia, Piscataway, N.J.), or pQE (Qiagen), which fuse glutathione S-transferase (GST), maltose binding protein, protein A, or poly-His, respectively, to the target recombinant protein.

Examples of suitable inducible non-fusion *E. coli* expression vectors include pTrc (Amann et al., (1988), *Gene*

69:301–315) and pETIId (Studier et al., Gene Expression Technology: Methods in Enzymology 185, Academic Press, San Diego, Calif. (1990) 60–89). One strategy to maximize recombinant protein expression in *E. coli* is to express the protein in a host bacteria with an impaired capacity to proteolytically cleave the recombinant protein. Another strategy is to alter the nucleic acid sequence of the nucleic acid to be inserted into an expression vector so that the individual codons for each amino acid are those preferentially utilized in *E. coli*. Such alteration of nucleic acid sequences of the invention can be carried out by standard DNA synthesis techniques.

In another embodiment, the expression vector is a yeast expression vector. Examples of vectors for expression in yeast *S. cerivisae* include pYepSec1 (Baldari et al., (1987), *EMBO J* 6:229–234), pMFa (KurJan et al., (1982), *Cell* 30:933–943), pJRY88 (Schultz et al., (1987), *Gene* 54:113–123), pYES2 (Invitrogen Corporation, San Diego, Calif.), and pPicZ or *Pichia* (Invitrogen Corp, San Diego, Calif.).

Alternatively, the expression vector is a baculovirus expression vector. Baculovirus vectors available for expression of proteins in cultured insect cells include, but are not limited to, the pAc series (Smith et al., (1983), *Mol. Cell Biol.* 3:2156–2165) and the pVL series (Lucklow et al., (1989), *Virology* 170:31–39).

Alternatively, the expression vector is an insect expression vector. A variety of insect cell expression vectors can be used to express recombinant protease PRSS11-L in insect cells. Commercially available insect cell expression vectors useful for recombinant protease PRSS11-L expression, include, but are not limited to, pBlueBacII (Invitrogen).

In yet another embodiment, the expression vector is a mammalian expression vector. When used in mammalian cells, the expression vector's control functions are often provided by viral regulatory elements. For example, commonly used promoters are derived from polyoma, Adenovirus 2, cytomegalovirus and Simian Virus 40. Examples of mammalian expression vectors include, but are not limited to, pCDM8 (Seed (1987) Nature 329:840) and pMT2PC (Kaufinan et al., (1987), *EMBO J.* 6:187–195). Commercially available mammalian expression vectors which can be suitable for recombinant protease PRSS11-L expression, include, but are not limited to, pMAMneo (Clontech), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and lZD35 (ATCC 37565).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., (1987), *Genes Dev.* 1:268–277), lymphoid-specific promoters (Calame et al, (1988), *Adv. Immunol.* 43:235–275), in particular promoters of T cell receptors (Winoto et al, (1989), *EMBO J* 8:729–733) and immunoglobulins (BaneiJi et al., (1983), *Cell* 33:729–740; Queen et al., (1983), *Cell* 33:741–748), neuron-specific promoters (e.g., the neurofilament promoter; Byme et al., (1989), *Proc. Natl. Acad. Sci. USA* 86:5473–5477), pancreas-specific promoters (Edlund et al., (1985), *Science* 230:912–916), and mammary gland-specific promoters (e.g., milk whey promoter; U.S. Pat. No. 4,873,316 and European Application Publication No. 264,166). Developmentally-regulated promoters also include, for example, the marine hox promoters (Kessel et al., (1990), *Science* 249:374–379) and the beta-fetoprotein promoter (Campes et al., (1989), *Genes Dev.* 3:537–546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Specifically designed vectors allow the shuttling of DNA between hosts such as bacteria-yeast or bacteria-animal cells or bacteria-fungal cells or bacteria-invertebrate cells. Numerous cloning vectors are known to those of skill in the art and the selection of an appropriate cloning vector is a matter of choice. For other suitable expression systems for both prokaryotic and eukaryotic cells see chapters 16 and 17 of Maniatis et al., supra.

Recombinant Host Cells

Another aspect of the invention pertains to recombinant host cells into which a recombinant expression vector of the invention has been introduced.

Cell lines derived from mammalian species which can be suitable for transfection and which are commercially available, include, but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), *Drosophila* or murine L-cells, and HEK-293 (ATCC CRL1573), and monkey kidney cells.

Vector DNA can be introduced into prokaryotic or eukaryotic cells via conventional transformation or transfection techniques. As used herein, the terms "transformation" or "transfection" refers to a process by which cells take up foreign DNA and may or may not integrate that foreign DNA into their chromosome. Transfection can be accomplished, for example, by various techniques including calcium phosphate or calcium chloride co-precipitation, DEAE-dextran-mediated transfection, lipofection, or electroporation, protoplast fusion. Suitable methods for transforming or transfecting host cells can be found in Maniatis et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

In another embodiment, the expression characteristics of an endogenous (e.g., PRSS11-L) nucleic acid within a cell, cell line or microorganism, can be modified by inserting a DNA regulatory element heterologous to the endogenous gene of interest into the genome of a cell, a stable cell line or a cloned microorganism such that the inserted regulatory element is operatively linked with the endogenous gene (e.g., PRSS11-L) and controls, modulates or activates the endogenous gene. For example, endogenous PRSS11-L which is normally "transcriptionally silent", i.e., PRSS11-L gene which is normally not expressed, or is expressed only at very low levels in a cell line or microorganism, can be activated by inserting a regulatory element which is capable of promoting the expression of a normally expressed gene product in that cell line or microorganism. Alternatively, transcriptionally silent, endogenous PRSS11-L genes can be activated by insertion of a promiscuous regulatory element that is active across cell types.

A heterologous regulatory element can be inserted into a stable cell line or cloned microorganism, such that it is operatively linked with and activates expression of endogenous PRSS11-L genes, using techniques, such as targeted homologous recombination, which is well known to those of skill in the art, and described e.g., in Chappel, U.S. Pat. No. 5,272,071; PCT publication No. WO 91/06667, published May 16, 1991.

The recombinant host cells of the invention can also be used to produce nonhuman transgenic animals. For example, in one embodiment, a host cell of the invention is a fertilized oocyte or an embryonic stem cell into which a sequence encoding a polypeptide of the invention has been introduced. Such host cells can then be used to create non-human transgenic animals in which exogenous sequences encoding a polypeptide of the invention have been introduced into their genome or homologous recombinant animals in which endogenous sequences encoding a polypeptide of the invention have been altered. Such animals are useful for studying the function and/or activity of the polypeptide and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. Clones of the non-human transgenic animals can also be produced according to the methods described in Wilmut et al., (1997), *Nature* 3 8 5:810–813 and PCT Publication NOS. WO 97/07668 and WO 97/07669.

Protease PRSS11-Like Polypeptides

One other aspect of the invention pertains to substantially purified PRSS11-L polypeptides.

Isolated Polypeptides of the Present Invention

In one embodiment, the invention provides a substantially purified polypeptide having S2 serine protease activity, comprising an amino acid sequence having at least a 90% and preferably a 95% sequence identity to amino acid 1 to 9 of SEQ ID NO: 2. The identity and similarity between two polypeptides can be determined using the method described supra.

In a preferred embodiment, the polypeptides of the present invention comprise an amino acid sequence that is identical to SEQ ID NO:2.

The isolated polypeptide of the invention includes chimeric or fusion proteins. As used herein, a "chimeric protein" or "fusion protein" comprises all or part (preferably biologically active) of a polypeptide of the invention operably linked to a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the N-terminus or C-terminus of the polypeptide of the invention.

One useful fusion protein is a HAHis fusion protein in which the polypeptide of the invention is fused at the C-terminus to a tag made of HA and poly His. Such fusion proteins facilitate the detection and purification of a recombinant polypeptide of the invention.

In another embodiment, the fusion protein contains a heterologous signal sequence at its N-terminus. A signal sequence from another protein, for example, the gp67 signal sequence of the baculovir-Us envelope protein (Current Protocols in Molecular Biology, Ausubel et al., eds., John Wiley & Sons, 1992), the signal sequences of melittin and human placental alkaline phosphatase (Stratagene; La Jolla, Calif.), and useful prokaryotic signal sequences include the phoA secretory signal and the protein A secretory signal (Pharmacia Biotech; Piscataway, N.J.), can all be used as a heterologous signal sequence to direct the secretion of PRSS11-L.

In yet another embodiment, the fusion protein is an immunoglobulin fusion protein in which all or part of a polypeptide of the invention is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction can be useful therapeutically, both for treating proliferative and differentiative disorders and for modulating (e.g. promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands.

Expression And Isolation of Protease PRSS11-L

The invention pertains to methods of expressing or isolating a polypeptide of the invention.

As used herein, "recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

In one embodiment, the polypeptide can be isolated from cells or tissue sources that express it naturally by an appropriate purification scheme using standard protein purification techniques. In another embodiment, polypeptides of the invention are produced by recombinant DNA techniques. Alternatively, a polypeptide of the invention can be synthesized in an in vitro translation and/or transcription system. Further alternatively, a polypeptide of the invention can be synthesized chemically using standard peptide synthesis techniques.

Polypeptides of the invention can be recombinantly expressed by cloning DNA molecules of the invention into an expression vector described supra, introducing such a vector into prokaryotic or eukaryotic host cells described herein, and growing the host cell under conditions suitable for production of recombinant protease PRSS11-L protein. The expression vector-containing cells are clonally propagated and individually analyzed to determine whether they produce protease PRSS11-L protein. Identification of protease PRSS11-L expressing host cell clones can be done by several means, including, but not limited to, immunological reactivity with anti-protease PRSS11-L antibodies, and the presence of host cell-associated protease PRSS11-L activity. The selection of the appropriate growth conditions and recovery methods are within the skill of the art. Techniques for recombinantly expressing a polypeptide are fully described in Maniatis, T, et al., supra, and are well known in the art.

Polypeptides of the invention can also be produced using an in vitro translation and/or transcription system. Such methods are known to those skilled in the art. For example, synthetic PRSS11-L mRNA or mRNA isolated from protease PRSS11-L producing cells can be efficiently translated in various cell-free systems, including, but not limited to, wheat germ extracts and reticulocyte extracts. Alternatively, the coding sequence of PRSS11-L cDNA can be cloned under the control of a T7 promoter. Then, using this construct as the template, PRSS11-L protein can be produced in an in vitro transcription and translation system, for example using a TNT T7 coupled Reticulocyte Lysate System such as that commercially available from Promega (Madison, Wis.).

Polypeptides of the invention can also be produced by chemical synthesis, such as solid phase peptide synthesis on an automated peptide synthesizer, using known amino acid sequences or amino acid sequences derived from the DNA sequence of the genes of interest. Such methods are known to those skilled in the art.

Following expression of protease PRSS11-L in a recombinant host cell, protease PRSS11-L protein can be recovered to provide purified protease PRSS11-L in active form. Such methods are known to those skilled in the art. For example, protease PRSS11-L from natural host cells, or recombinant protease PRSS11-L from recombinant host can be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography, lectin chromatography, HPLC, and FPLC, and antibody/ligand affinity chromatography.

Protease PRSS11-L can be separated from other cellular proteins by use of an immunoaffinity column made with monoclonal or polyclonal antibodies specific for full-length nascent protease PRSS11-L, polypeptide fragments of protease PRSS11-L or protease PRSS11-L subunits. Protease PRSS11-L antibody affinity columns are made by adding the antibodies to a gel support such that the antibodies form covalent linkages with the gel bead support. Prefered covalent linkages are made through amine, aldehyde, or sulfhydryl residues contained on the antibody. Methods to generate aldehydes or free sulfydryl groups on antibodies are well known in the art; amine groups are reactive with, for example, N-hydroxysuccinimide esters. The affinity resin is then equilibrated in a suitable buffer, for example phosphate buffered saline (pH 7.3), and the cell culture supernatants or cell extracts containing protease PRSS11-L or protease PRSS11-L subunits are slowly passed through the column. The column is then washed with the buffer until the optical density ($A_{280}$) falls to background, then the protein is eluted by changing the buffer condition, such as by lowering the pH using a buffer such as 0.23 M glycine-HCl (pH 2.6). The purified protease PRSS11-L protein is then dialyzed against a suitable buffer such as phosphate buffered saline.

The affinity column purification can also be performed using other proteins or compounds that bind to PRSS11-L tightly.

Antibodies for Polypeptide of the Present Invention

Another aspect of the invention pertains to antibodies binding specifically to a polypeptide of the invention. The term "antibody" as used herein refers to immunoglobulin molecules and immunologically active portions of immunoglobulin molecules, i.e., molecules that contain an antigen binding site which specifically binds an antigen, such as a polypeptide of the invention, e.g., an epitope of a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and $F(ab)_2$ fragments which can be generated by treating the antibody with an enzyme such as pepsin.

In various embodiments, the substantially purified antibodies of the invention, or fragments thereof, can be human, non-human, chimeric and/or humanized antibodies. Such antibodies of the invention can be, but are not limited to, goat, mouse, rat, sheep, horse, chicken, or rabbit, antibodies. In addition, the invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. The term "polyclonal antibody" refers to antibodies directed against a polypeptide or polypeptides of the invention capable of immunoreacting with more than one epitopes. Particularly preferred polyclonal antibody preparations are ones that contain only antibodies directed against a polypeptide or polypeptides of the invention.

The term "antigen" as used herein refers to a molecule containing one or more epitopes that will stimulate a host's immune system to make a humoral and/or cellular antigen-specific response. The term is also used herein interchangeably with "immunogen."

The term "epitope" as used herein refers to the site on an antigen or hapten to which a specific antibody molecule binds. The term is also used herein interchangeably with "antigenic determinant" or "antigenic determinant site." An isolated polypeptide consisting of amino acid sequence 1 to 9 of SEQ ID NO: 2, can be used as an immunogen to generate antibodies using standard techniques for polyclonal and monoclonal antibody preparation. The immunogen can be obtained using protein expression and isolation techniques known to those skilled in the art, such as recombinant expression from a host cell, chemical synthesis of proteins, or in vitro transcription/translation. Particularly preferred immunogen compositions are those that contain no other animal proteins such as, for example, immunogen recombinantly expressed from a non-animal host cell, i.e., a bacterial host cell.

Polyclonal antibodies can be raised by immunizing a suitable subject animals such as mice, rats, guinea pigs, rabbits, goats, horses and the like, with rabbits being preferred, with the immunogen of the invention with or without an immune adjuvant. Preimmune serum is collected prior to the first immunization. Each animal receives between about 0.001 mg and about 1000 mg of the immunogen associated with or without an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of protease PRSS11-L in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunizaiton. Those animals receiving booster injections are generally given an equal amount of the antigen in Freund's incomplete adjuvant by the same route. Booster injections are given at about three-week intervals until maximal titers are obtained. At about 7 days after each booster immunization or about weekly after a single immunization, the animals are bled, the serum collected, and aliquots are stored at about −20° C.

Monoclonal antibodies (mAb) are prepared by immunizing inbred mice, preferably Balb/c, with the immunogen. The mice are immunized by the IP or SC route with about 0.001 mg to about 1.0 mg, preferably about 0.1 mg, of the immunogen in about 0.1 ml buffer or saline incorporated in an equal volume of an acceptable adjuvant, as discussed above. Freund's adjuvant is preferred, with Freund's complete adjuvant being used for the initial immunization and Freund's incomplete adjuvant used thereafter. The mice receive an initial immunization on day 0 and are rested for about 2 to about 30 weeks. Immunized mice are given one or more booster immunizations of about 0.001 to about 1.0 mg of protease PRSS11-L in a buffer solution such as phosphate buffered saline by the intravenous (IV) route. Lymphocytes, from antibody positive mice, preferably spleenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag 4-1; MPC-11; S-194 and Sp2/0, with Sp2/0 being generally preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using protease PRSS11-L as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973 or by the technique of limited dilution.

Monoclonal antibodies are produced in vivo by injection of pristane primed Balb/c mice, approximately 0.5 ml per mouse, with about $1\times10^6$ to about $6\times10^6$ hybridoma cells at least about 4 days after priming. Ascites fluid is collected at approximately 8–12 days after cell transfer and the monoclonal antibodies are purified by techniques known in the art.

Monoclonal Ab can also be produced in vitro by growing the hydridoma in tissue culture media well known in the art. High density in vitro cell culture can be conducted to produce large quantities of mAbs using hollow fiber culture techniques, air lift reactors, roller bottle, or spinner flasks culture techniques well known in the art. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of protease PRSS11-L in body fluids or tissue and cell extracts.

The antibody molecules can be isolated from the mammal (e.g., from the blood) or culture cells and further purified by well-known techniques, such as protein A chromatography to obtain the IgG fraction. Alternatively, antibodies specific for a protein or polypeptide of the invention can be selected for (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those on the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb—and a human immunoglobulin constant region (See, e.g., Cabilly et al., U.S. Pat. No. 4,816,567). Humanized antibodies are antibody molecules from non-human species having one or more complementarily determining regions (CDRS) from the non-human species and a framework region from a human immunoglobulin molecule (See, e.g., Queen, U.S. Pat. No. 5,585,089). Such chimeric and humanized monoclonal antibodies can be produced by recombinant DNA techniques known in the art, for example using methods described in PCT Publication No. WO 87/02671, which is incorporated herein by reference in its entirety.

Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg et al., (1995), *Int. Rev. Immunol.* 13:65–93).

Completely human antibodies which recognize a selected epitope can be generated using a technique referred to as "guided selection". In this approach a selected non-human monoclonal antibody, e.g., a mouse antibody, is used to guide the selection of a completely human antibody recognizing the same epitope (Jespers et al., (1994), *Bioltechnology* 12:899–903).

The antibody of the invention (e.g., monoclonal antibody) can be used to isolate the polypeptide of the invention by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetyleholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H. Further, an antibody (or fragment thereof) can be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, I-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCN-LJ), cyclothosphamide, busulfan, dibromomannitol, streptozotocin, mitomycin C, and cis-dichlorodiamine platinum (11) (DDP) cisplatin), anthracyclines (e.g., daunorubicin (formerly daunomycin) and doxorabicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety can be a protein or polynucleotide possessing a desired biological activity. Alternatively, an antibody can be conjugated to a second antibody to form an antibody heteroconjugate as described by Segal in U.S. Pat. No. 4,676,980.

Methods of Detection

The present invention also relates to methods of detecting a polypeptide or nucleic acid of the invention in a biological sample. Such assay can be used for diagnostic purpose.

In one embodiment, the invention provides a method of detecting a nucleic acid molecule of a PRSS11-L gene, comprising the step of contacting a biological sample with a nucleic acid probe that hybridizes to the PRSS11-L nucleic acid molecule under stringent conditions and detecting the probe-nucleic acid molecule complex. A preferred agent for detecting mRNA or genomic DNA of a PRSS11-L gene is a labeled nucleic acid probe capable of hybridizing to mRNA or genomic DNA encoding a polypeptide of the invention as described supra.

In another embodiment, the invention provides a method of detecting a PRSS11-L protein, comprising the step of contacting a biological sample with an antibody that selectively binds to amino acids 1 to 9 of SEQ ID NO: 2, and detecting the protein-antibody complex. A preferred agent for detecting a polypeptide of the invention is an labeled antibody capable of binding to amino acids 1 to 9 of SEQ ID No: 2 as described supra.

Proteins, mRNAs, and genomic DNAs, can be detected in vitro as well as in vivo. For example, in vitro techniques for detection of mRNA include Northern hybridization, in situ hybridization, and RT-PCR. In vitro techniques for detection of a polypeptide of the invention include enzyme linked immunosorbent assays (ELISAs), Western blots, immunoprecipitations and immunofluorescence. In vitro techniques for detection of genomic DNA include Southern hybridization and PCR. Furthermore, in vivo techniques for detection of mRNA include transcriptional fusion infra. In vivo techniques for detection of a polypeptide of the invention include translational fusion infra, or introducing into a subject a labeled antibody directed against the polypeptide. For example, the antibody can be labeled with a radioactive marker whose presence and location in a subject can be detected by standard imaging techniques.

The invention also encompasses kits for detecting the presence of a polypeptide or nucleic acid of the invention in a biological sample (a test sample). Such kits can be used to determine if a subject is suffering from or is at increased risk of developing a disorder related to PRSS11-L. Such a kit preferably comprises a compartmentalized carrier suitable to hold in close confinement at least one container. The carrier further comprises reagents such as recombinant PRSS11-L protein or anti-PRSS11-L antibodies suitable for detecting protease PRSS11-L. The carrier can also contain a means for detection such as labeled antigen or enzyme substrates or the like. For example, the kit can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). The kits can also include instructions for determining whether a test subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (e.g., an antibody attached to a solid support) which binds to a polypeptide of the invention; and, optionally; (2) a second, different antibody which binds to either the polypeptide or the first antibody and is conjugated to a detectable agent; and (3) a purified recombinant PRSS11-L protein as positive control.

For oligonucleotide-based kits, the kit can comprise, for example: (1) an oligonucleotide, e.g., a detectably labeled oligonucleotide, which hybridizes to a nucleic acid sequence encoding a polypeptide of the invention or (2) a pair of primers useful for amplifying a nucleic acid molecule encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

The invention also provides a method to detect genetic lesions or mutations in a PRSS11-L gene, thereby determining if a subject with the lesioned gene is at risk for a disorder related to PRSS11-L. In preferred embodiments, the methods comprises the steps of: (1) isolating PRSS11-L polynucleotide from a biological sample; (2) detecting a polynucleotide sequence of PRSS11-L in the sample; and (3) finding genetic lesions by comparing the sequence with that of the wild-type gene.

Examples of genetic mutations or genetic lesions of interest include, but are not limited to detection of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene. Methods for detecting these genetic lesions or mutations are well known in the art. There are a large number of assay techniques known in the art which can be used for detecting lesions in a gene, such as PCR reactions, restriction enzyme cleavage patterns, hybridizing a sample and control nucleic acids, sequencing reactions, alterations in electrophoretic mobility, selective oligonucleotide hybridization, selective amplification, and selective primer extension.

Method of Treatment Using Gene Therapy

The present invention provides methods of treating a subject at risk of or suffering from a disorder related to PRSS11-L by increasing or decreasing the expression of PRSS11-L using gene therapy.

In one embodiment, PRSS11-L antisense therapy can be used to decrease the expression of PRSS11-L in a cell. PRSS11-L antisense therapy can be particularly useful in decreasing PRSS11-L activity.

The principle of antisense based strategies is based on the hypothesis that sequence-specific suppression of gene expression can be achieved by intracellular hybridization between mRNA and a complementary antisense species. The formation of a hybrid RNA duplex can then interfere with the processing/transport/translation and/or stability of the target PRSS11-L mRNA. Hybridization is required for the antisense effect to occur. Antisense strategies can use a variety of approaches including the use of antisense oligonucleotides, injection of antisense RNA and transfection of antisense RNA expression vectors. Phenotypic effects induced by antisense hybridization to a sense strand are based on changes in criteria such as protein levels, protein activity measurement, and target mRNA levels.

An antisense nucleic acid can be complementary to an entire coding strand of a PRSS11-L gene, or to only a portion thereof. An antisense nucleic acid molecule can also be complementary to all or part of a non-coding region of the coding strand of a PRSS11-L gene. The non-coding regions ("5' and 3'untranslated regions") are the 5' and 3' sequences which flank the coding region and are not translated into amino acids. Preferably, the non-coding region is a regulatory region for the transcription or translation of the PRSS11-L gene.

An antisense oligonucleotide can be, for example, about 15, 25, 35, 45 or 65 nucleotides or more in length taken from the complementary sequence of SEQ ID NO:1. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxytnethylaminomethyl-2-thiouridine, 5-carboxymethylaminomethyluracil, dihydrouracil, beta-D-galactosylqueosine, inosine, N6-isopentenyladenine, I-methylguanine, 1-methylinosine, 2,2-dimethylguanine, 2-methyladenine, 2-methylguanine, 3-methylecytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. An antisense nucleic acid molecule can be a CC-anomeric nucleic acid molecule. A CC-anomeric nucleic acid molecule forms specific double-stranded hybrids with complementary RNA in which, contrary to the usual P-units, the strands run parallel to each other (Gaultier et al. (1987) Nucleic Acids Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215: 327–330).

Alternatively, the antisense nucleic acid can also be produced biologically using an expression vector into which a nucleic acid has been subcloned in an antisense orientation as described supra. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. To achieve sufficient intracellular concentrations of the antisense molecules, vector constructs in which the antisense nucleic acid molecule is placed under the control of a strong pol II or pol III promoter are preferred. For a discussion of the regulation of gene expression using antisense genes see Weintraub et al. (1985, Trends in Genetics, Vol. 1(1), pp. 22–25).

Typically, antisense nucleic acid is administered to a subject by microinjection, liposome encapsulation or generated in situ by expression from vectors harboring the antisense sequence. An example of a route of administration of antisense nucleic acid molecules includes direct injection at a tissue site. The antisense nucleic acid can be ligated into viral vectors that mediate transfer of the antisense nucleic acid when the viral vectors are introduced into host cells. Suitable viral vectors include retrovirus, adenovirus, adeno-associated virus, herpes virus, vaccinia virus, polio virus and the like. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens.

Once inside the cell, antisense nucleic acid molecules hybridize with or bind to cellular mRNA and/or genomic DNA encoding a PRSS11-L protein to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix.

In a preferred embodiment, when it is beneficial to decrease PRSS11-L activity, the method of decreasing the expression of PRSS11-L in a subject in need thereof involves the use of small interfering RNA (siRNA).

In several organisms, introduction of double-stranded RNA has proven to be a powerful tool to suppress gene expression through a process known as RNA interference. Many organisms possess mechanisms to silence any gene when double-stranded RNA (dsRNA) corresponding to the gene is present in the cell. The technique of using dsRNA to reduce the activity of a specific gene was first developed using the worm *C. elegans* and has been termed RNA interference, or RNAi (Fire, et al., (1998), *Nature* 391: 806–811). RNAi has since been found to be useful in many organisms, and recently has been extended to mammalian cells in culture (see review by Moss, (2001), *Curr Biol* 11: R772–5).

An important advance was made when RNAi was shown to involve the generation of small RNAs of 21–25 nucleotides (Hammond et al., (2000) *Nature* 404: 293–6; Zamore et al., (2000) *Cell* 101: 25–33). These small interfering RNAs, or siRNAs, can initially be derived from a larger dsRNA that begins the process, and are complementary to the target RNA that is eventually degraded. The siRNAs are themselves double-stranded with short overhangs at each end; they act as guide RNAs, directing a single cleavage of the target in the region of complementarity (Elbashir et al., (2001) *Genes Dev* 15: 188–200).

Methods of producing siRNA of generally 21 to 23 nucleotides (nt) in length from an in vitro system and use of the siRNA to interfere with mRNA of a gene in a cell or organism are described in WO0175164 A2.

The siRNA can also be made in vivo from a mammalian cell using a stable expression system. A new vector system, named PSUPER, that directs the synthesis of small interfering RNAs (siRNAs) in mammalian cells, was recently reported (Brummelkamp et al., (2002) *Science* 296: 550–3.).

To produce pSUPER, the H1-RNA promoter was cloned in front of the gene specific targeting sequence (19-nt sequences from the target transcript separated by a short spacer from the reverse complement of the same sequence) and five thymidines (T5) as a termination signal. The resulting transcript is predicted to fold back on itself to form a 19-base pair stem-loop structure, resembling that of *C. elegans* Let-7. The size of the loop (the short spacer) is preferably 9 bp. A small RNA transcript lacking a polyadenosine tail, with a well-defined start of transcription and a termination signal consisting of five thymidines in a row (T5) was produced. Most importantly, the cleavage of the transcript at the termination site is after the second uridine yielding a transcript resembling the ends of synthetic siRNAs, that also contain two 3' overhanging T or U nucleotides. The siRNA expressed from pSUPER is able to knock down gene expression as efficiently as the synthetic siRNA.

The present invention provides a method of decreasing the expression of PRSS11-L in a cell of a subject in need thereof, comprising the steps of (a) introducing siRNA that targets the mRNA of the PRSS11-L gene for degradation into the cell of the subject; (b) maintaining the cell produced in (a) under conditions under which siRNA interference of the mRNA of the PRSS11-L gene in the cell of the subject occurs. The siRNA can be produced chemically via nucleotide synthesis, from an in vitro system similar to that described in WO0175164, or from an in vivo stable expression vector similar to pSUPER described herein. The 51RNA can be administered similarly as that of the antisense nucleic acids described herein.

In another embodiment, PRSS11-L gene therapy can be used to increase the expression of PRSS11-L by introducing a nucleic acid molecule capable of expressing a PRSS11-L protein into the cells of a subject. PRSS11-L gene therapy can be particularly useful for the treatment of diseases where it is beneficial to elevate PRSS11-L activity.

The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject, and returning the genetically engineered cell(s) to the subject. The functional copy of the gene is under operable control of regulatory elements which permit expression of the gene in the genetically engineered cell (s). Numerous transfection and transduction techniques as well as appropriate expression vectors are well known to those of ordinary skill in the art, some of which are described in PCT application WO95/00654. In vivo gene therapy uses vectors such as adenovirus, retroviruses, vaccinia virus, bovine papilloma virus, and herpes virus such as Epstein-Barr virus. Gene transfer could also be achieved using non-viral means requiring infection in vitro. This would include calcium phosphate, DEAE dextran, electroporation, and protoplast fusion. Targeted liposomes can also be potentially beneficial for delivery of DNA into a cell.

For example, a DNA molecule encoding the PRSS11-L protein, is first cloned into a retroviral vector. The expression of PRSS11-L protein from the vector is driven from its endogenous promoter or from the retroviral long terminal repeat or from a promoter specific for certain target cells. The vector is then introduced into a cell of a subject to successfully express PRSS11-L proteins in the target cells. The gene is preferably delivered to those cells in a form which can be used by the cell to encode sufficient protein to provide effective function. Retroviral vectors are often a preferred gene delivery vector for gene therapy especially because of their high efficiency of infection and stable integration and expression. Alternatively, PRSS11-L DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo PRSS11-L gene therapy. Protocols for molecular methodology of gene therapy suitable for use with the PRSS11-L gene are described in Gene Therapy Protocols, edited by Paul D. Robbins, Human press, Totowa N.J., 1996.

During treatment, the effective amount of nucleic acid molecules of the invention administered to individuals can vary according to a variety of factors including type, species, age, weight, sex and medical condition of the patient; the severity of the condition to be treated; the route of administration; the renal and hepatic function of the patient; and the particular nucleic acid molecule thereof employed. A physician or veterinarian of ordinary skill can readily determine and prescribe the effective amount required to prevent, counter or arrest the progress of the condition. Optimal precision in achieving concentrations within the range that yields efficacy without toxicity requires a regimen based on the kinetics of the nucleic acid molecule's availability to target sites. This involves a consideration of the distribution, equilibrium, and elimination of the nucleic acid molecule involved in gene therapy.

The gene therapy disclosed herein can be used alone at appropriate dosages defined by routine testing in order to obtain optimal increase or decrease of the protease PRSS11-L activity while minimizing any potential toxicity. In addition, co-administration or sequential administration of other agents may be desirable. The dosages of administration are adjusted when several agents are combined to achieve desired effects. Dosages of these various agents can be independently optimized and combined to achieve a synergistic result wherein the pathology is reduced more than it would be if either agent were used alone.

Methods of Identifying Modulators of PRS11-L

"Inhibitors", "activators", and "modulators" of PRSS11-L refer to inhibitory or activating molecules identified using in vitro and in vivo binding assays for PRSS11-L. Preferably by measuring the serine protease activity of PRSS11-L, the binding affinity of PRSS11-L to other proteins, or the chaperon activity of PRSS11-L.

In particular, "inhibitors" refer to compounds that decrease, prevent, inactivate, desensitize or down regulate PRSS11-L expression or activity. "Activators" are compounds that increase, activate, facilitate, sensitize or up regulate PRSS11-L expression or activity. "Modulators" include both the "inhibitors" and "activators".

The compound identification methods can be performed using conventional laboratory formats or in assays adapted for high throughput. The term "high throughput" refers to an assay design that allows easy screening of multiple samples simultaneously, and can include the capacity for robotic manipulation. Another desired feature of high throughput assays is an assay design that is optimized to reduce reagent usage, or minimize the number of manipulations in order to achieve the analysis desired. Examples of assay formats include 96-well or 384-well plates, levitating droplets, and "lab on a chip" microchannel chips used for liquid handling experiments. It is well known by those in the art that as miniaturization of plastic molds and liquid handling devices are advanced, or as improved assay devices are designed, that greater numbers of samples can be performed using the design of the present invention.

Candidate compounds encompass numerous chemical classes, although typically they are organic compounds. Preferably, they are small organic compounds, i.e., those having a molecular weight of more than 50 yet less than about 2500. Candidate compounds comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate compounds can comprise cyclic carbon or heterocyclic structure and/or aromatic or polyaromatic structures substituted with one or more of the above-identified functional groups. Candidate compounds also can be biomolecules such as peptides, saccharides, fatty acids, sterols, isoprenoids, purines, pyrimidines, derivatives or structural analogs of the above, or combinations thereof and the like. Where the compound is a nucleic acid, the compound typically is a DNA or RNA molecule, although modified nucleic acids having non-natural bonds or subunits are also contemplated.

Candidate compounds are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Candidate compounds can also be obtained using any of the numerous approaches in combinatorial library methods known in the art, including: biological libraries; spatially addressable parallel solid phase or solution phase libraries: synthetic library methods requiring deconvolution; the "one-bead one-compound" library method; and synthetic library methods using affinity chromatography selection (Lam (1997) *Anticancer Drug Des.* 12:145) Alternatively, libraries of natural compounds in the form of bacterial, fungal, plant and animal extracts are available or readily produced. Additionally, natural and synthetically produced libraries and compounds can be readily modified through conventional chemical, physical, and biochemical means.

Further, known pharmacological agents can be subjected to directed or random chemical modifications such as acylation, alkylation, esterification, amidification, etc. to produce structural analogs of the agents. Candidate compounds can be selected randomly or can be based on existing compounds that bind to and/or modulate the function of PRSS11-L protease. Therefore, a source of candidate agents is libraries of molecules based on known S2 serine protease activators or inhibitors, in which the structure of the compound is changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions. One of ordinary skill in the art in the preparation of combinatorial libraries can readily prepare such libraries based on the existing serine protease activators/inhibitors (see Abato et al., (1999), *J Med Chem.,* 42:4001–9; Zega et al., (2001), *Bioorg Med Chem,* 9:2745–56).

A variety of other reagents also can be included in the mixture. These include reagents such as salts, buffers, neutral proteins (e.g., albumin), detergents, etc. that can be used to facilitate optimal protein-protein and/or protein-nucleic acid binding. Such a reagent can also reduce non-specific or background interactions of the reaction components. Other reagents that improve the efficiency of the assay such as nuclease inhibitors, antimicrobial agents, and the like can also be used.

Examples of methods for the synthesis of molecular libraries can be found in the art, for example in: Zuckermann et al. (1994). *J. Med. Chem.* 37:2678. Libraries of compounds can be presented in solution (e.g., Houghten. (1992) *Biotechniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. No. 5,571,698), plasmids (Cull et al. (1992) *Proc. Natl. Acad. Sci. USA* 89:1865–1869) or phage (see e.g., Scott and Smith (1990) *Science* 249:386–390).

Methods of Identifying a Compound that Modulates PRSS11-L Expression

As used herein, "a compound that modulates PRSS11-L expression" includes compounds that increase or decrease PRSS11-L gene transcription and/or translation. The invention provides a method of identifying such a compound, which comprises the steps of contacting a compound with a regulatory sequence of the PRSS11-L pacemaker gene or a cellular component that binds to the regulatory sequence; and determining the effect of the compound on the expression of a gene controlled by the regulatory sequence; wherein the regulatory sequence of the PRSS11-L gene is either within a host cell or in a cell-free system.

In a preferred embodiment, the method involves detecting activity of a regulatory sequence of the PRSS11-L gene in a target cell. The cell-based assay comprises the step of: (1) contacting a compound with a cell comprising a regulatory sequence for a PRSS11-L gene or a cellular component that binds to the regulatory sequence operably linked to PRSS11-L or a reporter gene; (2) measuring the effect of the compound on the expression of the PRSS11-L or the reporter gene; and (3) comparing the effect of the compound with that of a reference control. The target cell can be a native PRSS11-L containing cell cell, or a cell where the PRSS11-L gene has been introduced. The reference control preferably contain the vehicle in which the testing compound is dissolved. Several assay methods can be used to measure the effect of the compound on the expression of the PRSS11-L or reporter gene inside a cell. For example, gene or protein fusions comprising the regulatory sequence for a PRSS11-L coding sequence linked to a reporter gene can be used.

As used herein, "a reporter gene" refers to a gene whose gene product can be measured using conventional lab techniques. Such reporter genes include, but are not limited to, genes encoding green fluorescent protein (GFP), β-galactosidase, luciferase, chloramphenicol acetyltransferase, β-glucuronidase, neomycin phosphotransferase, and guanine xanthine phosphoribosyl-transferase.

The gene fusion is constructed such that only the transcription of the reporter gene is under control of the PRSS11-L regulatory sequence. The protein fusion is constructed so that both the transcription and translation of the reporter gene protein are under control of the PRSS11-L regulatory sequence. Preferably, a second gene or protein fusion comprising the same reporter but a different regulatory sequence (i.e., a regulatory sequence for a gene unrelated to PRSS11-L protease) can be used to increase the specificity of the assay. The effect of the compound on the expression of the reporter gene, such as GFP, can be measured by methods known to those skilled in the art. For example, the effect of the compound on expression of GFP can be measured as the effect of the compound on emissions of green fluorescence from the cell using a fluorometer. Alternatively, a cellular phenotype attributed to PRSS11-L protease, such as the protease activity of PRSS11-L, can also be used to measure the effect of the compound on the expression of the PRSS11-L protein. In addition, the effect of the compound can be assayed by measuring the amount of PRSS11-L mRNA or protein inside the cell directly using methods described infra (i.e., Northern Blot, RT-PCR, SDS-PAGE, Western Blot, etc).

Note that the cell-based method described herein not only identifies compounds that regulate PRSS11-L expression directly via binding to the regulatory sequence of the PRSS11-L gene, but also identifies compounds that regulate PRSS11-L expression indirectly via binding to other cellular components whose activities influence PRSS11-L expression. For example, compounds that modulate the activity of a transcriptional activator or inhibitor for PRSS11-L genes can be identified using the method described herein.

In another embodiment, the method involves a regulatory sequence of the PRSS11-L gene in a cell-free assay system. The cell-free assay comprises the step of: (1) contacting a compound with a regulatory sequence for a PRSS11-L gene or with a cellular component that binds to the regulatory sequence in a cell-free assay system; (2) measuring the effect of the compound on the expression of the PRSS11-L or reporter gene controlled by the regulatory sequence; and (3) comparing the effect of the compound with that of a reference control. The reference control contains only the vehicle in which the testing compound is dissolved. Examples of a cell-free assay system include in vitro translation and/or transcription systems, which are known to those skilled in the art. For example, the full length PRSS11-L cDNA, including the regulatory sequence, can be cloned into a plasmid. Then, using this construct as the template, PRSS11-L protein can be produced in an in vitro transcription and translation system. Alternatively, synthetic PRSS11-L mRNA or mRNA isolated from PRSSl11-L protein producing cells can be efficiently translated in various cell-free systems, including but not limited to wheat germ extracts and reticulocyte extracts. The effect of the compound on the expression of the PRSS11'-L or reporter genes controlled by the regulatory sequence can be monitored by direct measurement of the quantity of HCN or reporter mRNA or protein using methods described infra.

Methods of Identifying a Compound that Modulates PRSS11-L Biological Activity

As used herein, "a compound that modulates PRSS11-L biological activity" includes compounds that increase or decrease one or more biological activities of PRSS11-L. Such compounds include, but are not limited to, compounds: 1) that increase or decrease the serine protease activity of PRSS11-L; 2) that increase or decrease the protein stability of the PRSS11-L; 3) that increase or decrease the chaperon activity of PRSS11-L; or 4) that increase or decrease the binding affinity of PRSS11-L to other proteins. The present invention provides methods of identifying such a compound, comprising the steps of contacting a test compound with a PRSS11-L protein; and determining the effect of the compound on the biological activities of the PRSS11-L protein.

In one preferred embodiment, compounds that increase or decrease the protease activity of PRSS11-L can be identified by a method comprising the steps of: (1) contacting a test compound with a PRSS11-L protein and with a substrate that is cleavable by the PRSS11-L protease; and (2) determining whether the test compound increases or decreases the cleavage of said substrate by the PRSS11-L protease. While various appropriate substrates can be designed for use in the assay, such as case casein, preferably, a labeled peptidyl substrate comprising the PRSS11-L protease cleavage site, is used. Labeled substrates include, but are not limited to; substrate that is radiolabeled (Coolican et al., (1986), *J. Biol. Chem.* 261:4170–6), fluorometric (see Lonergan et al., (1995), *J. Food Sci.* 60:72–3, 78) or colorimetric (Buroker-Kilgore et al., (1993), *Anal. Biochem.* 208:387–92). Radioisotopes useful for use in the present invention include those well known in the art, specifically $^{125}I$, $^{131}I$, $^{3}H$, $^{14}C$, $^{35}S$, $^{32}P$, and $^{33}P$. Radioisotopes are introduced into the peptide by conventional means, such as iodination of a tyrosine residue, phosphorylation of a serine or threonine residue, or incorporation of tritium, carbon or sulfur using radioactive amino acid precursors. Zymography following SDS polyacrylamide gel electrophoresis (Wadstroem et al., (1973), *Sci. Tools* 20:17–21), as well as by fluorescent resonance energy transfer (FRET)-based methods (Ng et al., (1989), *Anal. Biochem.* 183:50–6) are also methods used to detect compounds that modulate protease PRSS11-L proteolytic activity. A variety of methods can be used to detect the label, depending on the nature of the label and other assay components. For example, the label can be detected while bound to the solid substrate or subsequent to separation from the solid substrate. Labels can be directly detected through optical or electron density, radioactive emissions, nonradiative energy transfers, etc. or indirectly detected with antibody conjugates, streptavidin-biotin conjugates, etc. Methods for detecting the labels are well known in the art.

Compounds that are agonists will increase the rate of substrate degradation and will result in less remaining substrate as a function of time. Compounds that are antagonists will decrease the rate of substrate degradation and will result in greater remaining substrate as a function of time. To examine the extent of inhibition or activation, samples or assays comprising a PRSS11-L protein and its substrate are treated with a potential activator or inhibitor compound and are compared to control samples without the test compound. Control samples (untreated with test compounds) are assigned a relative protease activity value of 100%. Inhibition of PRSS11-L protease activity is achieved when the protease activity value relative to the control is about 75%, preferably 50%, more preferably 25–0%. Activation of PRSS11-L protease activity is achieved when the HCN activity value relative to the control is 110%, more preferably 150%, most preferably at least 200–500% higher or 1000% or higher.

The measurement means of the method of the present invention can be further defined by comparing two cells, one containing a PRSS11-L protein and a second cell originating from the same clone but lacking the PRSS11-L protein. After both cells are contacted with the same test compound, differences in PRSS11-L protease activities between the two cells are compared. Similarly, the measurement means of the method of the present invention can be further defined by comparing two cell lysates derived from the above two cells. These techniques are also useful in establishing the background noise of these assays. One of ordinary skill in the art will appreciate that these control mechanisms also allow easy selection of cellular changes that are responsive to modulation of PRSS11-L protease activity.

The term "cell" refers to at least one cell, but includes a plurality of cells appropriate for the sensitivity of the detection method. Cells suitable for the present invention can be bacterial, yeast, or eukaryotic.

The term "cell lysate" refers to a collected of cellular components produced by the destructive process of lysing a cell or cells.

The present invention provides methods to screen for proteins that interact with PRSS11-L. PRSS11-L interacting proteins could represent potential substrates or more likely modulators of PRSS11-L function and would likely yield clues as to the overall function of the PRSS11-L gene product. Methods to assay for protein-protein interactions are known to those skilled in the art. For example, the yeast two-hybrid system provides methods for detecting the interaction between a first test protein and a second test protein, in vivo, using reconstitution of the activity of a transcriptional activator. One method is disclosed in U.S. Pat. No. 5,283,173; reagents are available from Clontech and Stratagene (San Diego, Calif.). Another alternative method is immunoaffinity purification. Recombinant PRSS11-L is incubated with labeled or unlabeled cell extracts and immunoprecipitated with anti-PRSS11-L antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing. Further, standard biochemical purification steps known to those skilled in the art can be used prior to microsequencing. Yet another alternative method is screening of peptide libraries for binding partners. Recombinant tagged or labeled PRSS11-L is used to select peptides from a peptide or phosphopeptide library which interact with PRSS11-L. Sequencing of the peptides leads to identification of consensus peptide sequences which might be found in interacting proteins.

In another preferred embodiment, binding assays can be used to identify a compound that binds to PRSS11-L protein, and potentially is capable of increasing or decreasing the biological activity of PRSS11-L protein. One exemplary method comprises the steps of: (a) incubating a test compound with a PRSS11-L protein and a labeled ligand for the PRSS11-L protein; (b) separating the PRSS11-L protein from unbound labeled ligand; and (c) identifying a compound that inhibits ligand binding to the subunit by a reduction in the amount of labeled ligand binding to the PRSS11-L. An example of the labeled ligand for PRSS11-L protein is a labeled PRSS11-L specific antibody as described supra. Preferably, a PRSS11-L host cell (recombinant or native) that expresses the PRSS11-L can be used for the binding assay. More preferably, cell lysates prepared from the PRSS11-L host cell can be used for the binding assay. Further preferably, a substantially purified PRSS11-L protein can be used for the binding assay.

Separation of the PRSS11-L protein from unbound labeled ligand can be accomplished in a variety of ways. Conveniently, at least one of the components is immobilized on a solid substrate, from which the unbound components can be easily separated. The solid substrate can be made of a wide variety of materials and in a wide variety of shapes, e.g., microtiter plate, microbead, dipstick, resin particle, etc. The substrate preferably is chosen to maximize signal to noise ratios, primarily to minimize background binding, as well as for ease of separation and cost.

Separation can be effected for example, by removing a bead or dipstick from a reservoir, emptying or diluting a reservoir such as a microtiter plate well, or rinsing a bead, particle, chromatographic column or filter with a wash solution or solvent. The separation step preferably includes multiple rinses or washes. For example, when the solid substrate is a microtiter plate, the wells can be washed several times with a washing solution that typically includes those components of the incubation mixture that do not participate in specific binding such as salts, buffer, detergent, non-specific protein, etc. Where the solid substrate is a magnetic bead, the beads can be washed one or more times with a washing solution and isolated using a magnet.

A wide variety of labels can be used to label the PRSS11-L ligand, such as those that provide direct detection (e.g., radioactivity, luminescence, optical or electron density, etc), or indirect detection (e.g., epitope tag such as the FLAG epitope, enzyme tag such as horseradish peroxidase, etc.).

In more than one embodiment of the above assay methods of the present invention, it can be desirable to immobilize either the polypeptide of the invention or its target molecule to facilitate separation of complexed from uncomplexed forms of one or both of the proteins, as well as to accommodate automation of the assay. Binding of a test compound to the polypeptide, or interaction of the polypeptide with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or A polypeptide of the invention, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the polypeptide of the invention or its target molecule can be immobilized utilizing conjugation of biotin and streptavidin.

Biotinylated polypeptide of the invention or target molecules can be prepared from biotin-NHS(N-hydroxy-suceinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the polypeptide of the invention or target molecules but which do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

The following examples illustrate the present invention without, however, limiting the same thereto. The contents of all references, patents and published patent applications cited throughout this application are hereby incorporated by reference.

EXAMPLE 1

Isolation of the Protease PRSS11-L cDNA

All molecular biological methods were in accordance with those previously described (Maniatis et al., (1989), 1–1626). Oligonucleotides were purchased from Ransom Hill Biosciences (Ransom Hill, Calif.) and all restriction endonucleases and other DNA modifying enzymes were from New England Biolabs (Beverly, Mass.) unless otherwise specified. All construct manipulations were confirmed by dye terminator cycle sequencing using Allied Biosystems 377 fluorescent sequencers (Perkin Elmer, Foster City, Calif.).

A recombinant phage containing a partial protease PRSS11-L cDNA was isolated from a human prostate library (Clontech, Palo Alto, Calif.). The insert, was subjected to sequence analysis and found to contain sequences encoding a novel S2 protease. Although this particular isolate was ~2-Kb, additional sequence was obtained by 5'-RACE (Frohman, (1991), *Methods Enzymol.* 218:340–362) using human prostate Marathon Ready cDNA (Clontech, Palo Alto, Calif.) and Native Pfu Polymerase (Stratagene, La Jolla, Calif.) in accordance with the manufacturer's recommendations. Two sequential 50 μl 20 cycle PCR reactions of 94° C. for 30 sec.; 60.0° C. for 30 sec; 72° C. for 3.0 min. The first set of reactions were performed using the Marathon adapter primer AP1 and SEQ ID NO.3: PRSS11-Like P1-L 5'-CAGCCGTGACCTTGAGCGTGTTG-3' and the second set of reactions used 5.0 μl of the product from the first reaction as a template, the Marathon adapter primer AP1 and SEQ ID NO.4: PRSS11-Like P2-L 5'-GGCCGAGTGACCCAGCAACAAC-3'. An approx.1.4-Kb DNA molecule was amplified from the second set PCR reaction as the 5'-RACE DNA. The full length PRSS11-L cDNA was obtained by combining the 5'-RACE DNA molecule with the original 2 kb isolate via a unique SacI restriction site. The nucleotide sequence of the reconstructed PRSS11-L cDNA was sequenced, and depicted in SEQ ID NO: 1.

The isolated PRSS11-L cDNA was found to contain an open reading frame of 1002 nucleotides excluding the TGA stop codon. The open reading frame is likely to be authentic since it is preceded by an in-frame TGA stop codon at position 657. This clone is also likely to contain the entire 3' untranslated region since a putative polyadenylation sequence (AATAAA) was identified just 25 nucleotides upstream from a 17 nucleotide poly A stretch. The deduced open reading frame encodes a PRSS11-L protein of 334 amino acids (SEQ ID NO:2), with an estimated molecular mass ($M_r$) of about 36-Kd.

The complete sequence of the isolated cDNA as well as the encoded protein was not known previously. A detailed comparison of the encoded protein sequence with entries of the Genbank database revealed that the encoded protein is homologous to the catalytic domains of human S2 serine proteases. The sequence shares 62.1% identity within a defined 327 nucleotide overlap to human S2 serine protease L56/PRSS11-L, and 53.3% identity in a 323 nucleotide overlap to another human S2 serine protease Omi/HtrA2. These human S2 serine proteases belong to a family of proteases that has striking conservation between eukaryotes and prokaryotes. Therefore, the isolated cDNA herein is designated as PRSS11-L (PRSS11-Like) and its encoded protein as PRSS11-L protein.

Sequence alignment revealed that PRSS11-L protein shared strong homology to the catalytic domains of the other two human S2 serine proteases (FIG. 1). Motifs shared by all three human S2 serine proteases are TNAHVV (SEQ ID NO: 30), DIA and GNSGGPLVNLDGEVIG (SEO ID NO: 31) within the catalytic domains with the catalytic triad residues H, D and S of protease PRSS11-L located at positions 72, 108 and 186, respectively (using the methionine initiator of the PRSS11-L sequence as number one) (FIG. 1). In addition, the catalytic domains of these three S2 proteases appears to be flanked by an SH3 domain at the amino terminus and a PDZ domain at the C-terminus, both domains are importantly involved protein-interaction (Mayer, (2000), *J. Cell Science* 114:1253–1263; Sheng et al., (2001), *Annu. Rev. Neurosci.* 24:1–29). Therefore, PRSS11-L can interact with other proteins through these interactions interfaces. It is formally possible that the PRSS11-L protein is initially synthesized as an inactive zymogen precursor, which requires one or more limitedc proteolytic cleavages to become active. Because PRSS11-L protein appears to lack any hydrophobic amino acid stretch consistent with either a signal sequence or transmembrane domain, it is not likely to be secreted or an integral membrane protein.

Other nucleotide sequences within sequence databases of Genbank (AY040094) and the dgene_na patent (AAA57359 WO200039149-A2; AAA57361 WO200039149-A2; AAZ52362 WO200021986-A2; AAS26920 WO200155441-A2; AAS26848 WO200155441-A2) were subsequently found to share some sequence identities with the PRSS11-L cDNA (SEQ ID NO:1). Sequence analysis confirmed that these nucleotide sequences yield distinct mRNAs, which encode proteins having divergent N-termini.

EXAMPLE 2

Confirmation of an Authentic PRSS11-L mRNA

The existence of an authentic mRNA corresponding to the PRSS11-L (SEQ ID NO:1) in human prostate tissue was confirmed by PCR using primers designed to flank the translational initiation site.

PCR was performed using primers designed to flank the translational initiation site. Specifically, primers SEQ ID NO:7,5'-GCAAGTCGGGCTGGGGTGTG-3', and SEQ ID NO:8,5'-CAGGGAGCTTTTTCTTGGGATGGA-3' were designed to produce a 962-bp fragment between positions 413 and 1374 of the PRSS11-L cDNA (SEQ ID NO:1). For this application human prostate Marathon Ready cDNA was used as the templates and the GC cDNA amplification kit (Clontech, Palo Alto, Calif.) were used in accordance with the manufacturer's recommendations. Two sequential 50 µl PCR reactions, one of 30 cycles and the second of 10 cycles using 94° C. for 30 sec.; 62.4° C. for 30 sec; 68° C. for 2.0 min. were performed. The PCR product was subcloned using the pGEM Easy TA cloning system (Promega) and subjected to sequence analysis. The analysis revealed a 962-bp fragment with 100 percent identity to the isolated PRSS11-L cDNA from human prostate between positions 413 and 1374 of SEQ ID NO:1. This result confirmed that indeed, an authentic mRNA, corresponding to the PRSS11-L (SEQ ID NO:1), does actually exist in human prostate tissue.

EXAMPLE 3

Tissue Distribution of The Protease PRSS11-L mRNA

The tissue distribution of the PRSS11-L mRNA was examined using commercially available human multiple-tissue Northern blots (Clontech, Palo Alto, Calif.). The ~1.4-Kb PRSS11-L 5'-RACE product supra was used as a hybridization probe for the blots. The $^{32}$P-radiolabelled probe detected a single mRNA of an approximately 3.0 kb, which is consistent with the size of the reconstructed PRSS11-L cDNA (SEQ ID NO:1). The PRSS11-L mRNA transcript is widely expressed in several tissues throughout the body. It is highly expressed in heart, ovary; moderately in small intestine, colon, stomach, thyroid, trachea, adrenal gland; weakly in skeletal muscle, placenta, lung, pancreas, thymus, prostate, testis and bone marrow; very weakly in liver, kidney, spleen, spinal cord and lymph node. The PRSS11-L protease mRNA does not appear to be expressed in human brain although this does not exclude the possibility of a low level of PRSS11-L expression in smaller subregions of the brain.

In comparison, Northern analysis of L56 expression in human tissues indicated that an approximate 2.3 kb transcript of L56 is strongly expressed in placenta, moderately in brain, liver and kidney, and weakly in lung, skeletal muscle, heart and pancreas (Zumbrunn et al., (1996), supra). In further comparison, Northern analysis of Omi expression in human tissues indicated that two distinct mRNA species of Omi, a major one of approximately 2.1 kb and aminor one of approximately 4.5 kb, are expressed strongly in placenta and pancreas and weakly in heart, brain, lung, liver, muscle and kidney (Faccio et al., (2000), supra).

EXAMPLE 3

Vectors for the Expression of Protease PRSS11-L

The protease PRSS11-L expression vectors were constructed using the baculovirus expression vector pFastBacl (Life Technologies, Gaithersberg, Md.) as described below.

The purified plasmid DNA containing the full-length protease PRSS11-L cDNA was used as a template in a 100 µl preparative PCR reaction using the Native Pfu Polymerase (Stratagene, La Jolla, Calif.) in accordance with the manufacturer's recommendations. Two primers, SEQ ID NO 5: PRSS11-L Xba-U 5'-CGTGTCTAGAGCCATG-CACCTGGCCCTTCCCGCC-3' and SEQ ID NO 6: PRSS11-L Xba-L 5'-GCGCTCTAGACATGACCACCT- CAGGTGCGA-3', which contained Xba I cleavable sites were used for the PCR reaction. The preparative PCR reaction was run for 18 cycles of 94° C. for 30 sec.; 62.2° C. for 30 sec; and 72° C. for 2.0 min. The PRSS11-L coding sequence (CDS) Xba DNA cassette, comprising the full-length coding sequence of PRSS11-L (from nucleotide 1011 to 2014 of SEQ ID NO:1) flanked by two XbaI cleavage sites, was amplified from the PCR reaction. It was phenol/$CHCl_3$ (1:1) extracted once, $CHCl_3$ extracted, and then EtOH precipitated with glycogen carrier (Boehringer Mannheim Corp., Indianapolis, Ind.). The precipitated pellet was rinsed with 70' EtOH, dried by vacuum, and resuspended in 80 μl $H_2O$, 10 μl 10 restriction buffer number 2 and 1 μl 100× BSA (New England Biolabs, Beverly, Mass.).

The isolated PRSS11-L Xba DNA cassette was digested for 3 hr. at 37° C. with 200 units Xba I restriction enzyme (New England Biolabs, Beverly, Mass.). The Xba I digested product was phenol/$CHCl_3$ (1:1) extracted once, $CHCl_3$ extracted, EtOH precipitated, rinsed with 70% EtOH, and dried by vacuum. For purification from contaminating template plasmid DNA, the product was electrophoresed through 1.0% low melting temperature agarose (Life Technologies, Gaithersberg, Md.) gels in TAE buffer (40 mM Tris-Acetate, 1 mM EDTA pH 8.3) and excised from the gel.

The construct, PRSS11-Like CDS-HAHISpFastBac, containing a HA6HIS epitope/affinity tag fused in frame to the C-termus of the PRSS11-L CDS, was obtained by in-gel ligations of an aliquot of the excised PRSS11-L CDS Xba I DNA cassette together with an Xba I digested, dephosphorylated and gel purified, modified pFastBacl baculovirus transplacement vector. The DNA sequence of the construct was confirmed by sequence analyses.

The PRSS11-Like CDS Xba I fragment was also subcloned into a modified pCINeo mammalian expression vector (Promega, Madison, Wis.) containing the green fluorescent protein with the C-terminal HAHIS epitope affinity tag. The resulting PRSS11-Like CDS-GFPHAHIS (pCINeo) construct expresses the recombinant PRSS11-L protein with GFP and HAHIS fused to its C-terminus in a transfected mammalian cell line.

A second mammalian expression construct F-L PRSS11-L CDS-GFPHAHIS (pCINeo) was created to examine the role of the long PRSS11-L 5'-untranslated region (5'-UTR) on the expression of PRSS11-L in in vivo cell culture transfection experiments. This construct contained the native PRSS11-L 5'-UTR and the PRSS11-L CDS fused in frame at its C-termus to the GFP HAHIS module. It was constructed following procedures similar to those of PRSS11-Like CDS-GFPHAHIS (pCINeo) construct.

EXAMPLE 4

Purification of Recombinant Protease PRSS11-L

The expression vector PRSS11-Like CDS-HAHISpFastBac was first transformed into a bacterial host cell, and amplified inside such a bacterial transformant cell. The vector was purified and verified by PCR confirmation in accordance with the manufacturer's recommendations. Subsequently, the expression vector was used to transfect Sf9 insect cells (ATCC CRL-1711). Several days later, conditioned media containing the recombinant protease PRSS11-L-CDS-HAHIS baculovirus was collected for viral stock amplification. PRSS11-L expression was confirmed by Western blotting analysis of recombinant baculovirus infected Sf9 cells using an anti-HA MoAb (Boehringer Mannheim Corp., Indianapolis, Ind.).

Sf9 cells growing in Sf-900 II SFM at a density of $2\times10^6$/ml were infected at a multiplicity of infection of 2 at 27° C. Approximately 72 h later, cells were harvested and homogenized in 50 mM $NaH_2PO_4$ (pH 8.0) and 300 mM NaCl by 30–40 strokes. The homogenate was mixed with Tween-20 at the final concentration of 0.3% and centrifuged for 20 min at 15,000 ×g for 30 min. The resulting supernatant was batch-bound to Ni-NTA agarose beads (Qiagen, Valencia, Calif.) for 30 min at 4° C. The mixture was packed into a column and washed with $NaH_2PO_4$ (pH 8.0), 300 mM NaCl, and 25 mM imidazole. Then, the NTA agarose bead-bound PRSS11-L CDS-HAHIS was transferred to a microcentrifuge tube in 50 mM Tris-HCl (pH 7.5) and 50 mM NaCl.

Samples of cell lysates or the purified protease PRSS11-L CDS-HAHIS, were denatured in the presence of sodiun duodecyl sulfate and the reducing agent β-mercaptoethanol by boiling, and analyzed by SDS-PAGE (Bio Rad, Hercules Calif.). Polyacrylamide gels were either stained with Coomassie Brilliant Blue or subjected to Western blot analysis. For Western blotting, gels were electrotransferred to Hybond ECL membranes (Amersham, Arlington Heights, Ill.). The HA-tagged PRSS11-L-CDS-HAHIS recombinant protein was detected with the anti-HA 12CA5 MoAb (Boehringer Mannheim). The secondary antibody was a goat-anti-mouse IgG (H+L), horseradish peroxidase-linked F(ab')2 fragment, (Boehringer Mannheim Corp., Indianapolis, Ind.) and was detected by the ECL kit (Amersham, Arlington Heights, Ill.).

EXAMPLE 5

Expression of Recombinant Protease PRSS11-L in Mammalian Cells

The two mammalian expression constructs encoding PRSS11-Like CDS-GFPHAHIS and F-L PRSS11-L CDS-GFPHAHIS were transiently transfected into HEK-293 cells. Forty hours later, green fluorescence resulting from the PRSS11-L-GFP-HAHis fusion protein was examined by microscopy, and cell lysates generated were subjected to Western blot analysis using the anti-HA 12CA5 MoAb (Boehringer Mannheim). This experiment demonstrated that the PRSS11-L protein was expressed in eukaryotic cells.

EXAMPLE 6

Cleavage of β-Casein by Purified Recombinant Proteases PRSS11-L

The serine protease activity of PRSS11-L was demonstrated herein.

The full length PRSS11-L cDNA was fused to a C-terminal HAHIS epitope/affinity tag in frame on a baculovirus expression vector. The recombinant PRSS11-L protein with HAHIS epitope/affinity tag at its carboxyl terminus was expressed in baculovirus-infected cells. The recombinant protein was detected by immunoblot analysis using anti-HA antibody. Consistent with that observed for *E. coli* HtrA and human HtrA (L56), a distinct set of lower molecular weight proteins is also evident by immunoblot analysis, implying autocatalytic activity of PRSS11-L. The proteolytic activity of PRSS11-L was further confirmed by its cleavage of casein.

To demonstrate the protease activity of PRSS11-L protein, 1 μg of purified PRSS11-L CDS-HAHIS bound to Ni-NTA agarose beads in 10 μl was incubated with 50 μg of β-caesin (Sigma, St Louis, Mo.) in 50 mM Tris-HCl (pH 7.5) and 50 mM NaCl. The total reaction was 100 μl. After 1 h incubation at 37° C., the mixture was spun briefly to pellet the PRSS11-L CDS-HAHIS bound to Ni-NTA agarose beads, and 25 μl of the supernatant was taken for SDS-PAGE analysis. The cleavage of β-caesin was visualized by staining with Coomassie Brilliant Blue. Bovine trypsin was used as a positive control of β-casein cleavage and negative controls represent parallel reactions of casein incubated with Ni-NTA agarose beads, used to purify an irrelevant protein from baculovirus infected Sf9 cells, also in 50 mM Tris-HCl (pH 7.5) and 50 mM NaCl.

EXAMPLE 7

Screening for Compounds that Modulates PRSS11-L Proteolytic Activity

Compounds that modulate the serine protease of the present invention are identified through screening for the acceleration, or more commonly, the inhibition of the proteolytic activity. Although in the present case casein cleavage activity is monitored by a PAGE assay, chromogenic or fluorogenic assays or other methods such as FRET to measure proteolytic activity as mentioned above, can be employed. Compounds are dissolved in an appropriate solvent, such as DMF, DMSO, methanol, and diluted in water to a range of concentrations usually not exceeding 100 μM and are typically tested, though not limited to, a concentration of 1000-fold the concentration of protease. The compounds are then mixed with the protein stock solution, prior to addition to the reaction mixture. Alternatively, the protein and compound solutions can be added independently to the reaction mixture, with the compound being added either prior to, or immediately after, the addition of the protease PRSS11-L protein.

EXAMPLE 8

PRSS11-L is a Novel Alternative Splice Variant of HtrA3

Following the provisional filing, a sequence was submitted within GenBank (GenBank Accession No. BC034390) having about 87% sequence identity with the PRSS11-Like cDNA [SEQ ID No: 1]. This sequence, which is predicted to encode human HtrA3, was identified from the N1H-MGC Project. Part of the sequence (nt 589–2242) shares 100% identity with part of the SEQ ID NO: 1 (nt 1038–2691). The 5' end of the sequence (nt 1–588) shares less than 45% sequence identity with that of the SEQ ID No: 1 (nt 1–1037). Although the deduced amino acid sequence (GenBank Protein Id No: AAH34390) shares 100% identity with the PRSS11-Like amino acid sequence [SEQ ID No: 2] at the C-terminal catalytic domain, the sequences have divergent N-termini and thus represent distinct polypeptides (FIG. 2).

More recently the isolation of the human HtrA3 cDNA has been published (Nie, G,-Y., et al., (2003). *Biochem. J.* 371:39–48) and these investigators isolated both a long and short isoform GenBank Accession Nos. AY280665 and AY280666, respectively), which have alternatively spliced C-termini. All of these GenBank submissions contain the same extended N-terminus, which contains a signal sequence suggesting that these forms are secreted. Significantly, the PRSS11-Like cDNA encodes a distinct form of polypeptide lacking this extended N-terminus, but containing the same catalytic domain, suggesting that it encodes a non-secreted intracellular isoform of HtrA3.

The PRSS11-Like genomic structure was determined to establish whether the PRSS11-Like cDNA [SEQ ID No:1] is a distinct splice variant of the HtrA3 gene. This was accomplished by aligning both the HtrA3 long form cDNA and the PRSS11-Like cDNA sequences against the genomic sequence, a BAC clone from human chromosome 4 (GenBank Accession No. AC113611). The sequence alignments indicated that the HtrA3 long form cDNA was composed of nine exons while the PRSS11-Like cDNA was composed of eight exons (FIG. 3). The HtrA3 long form cDNA and the PRSS11-Like cDNA shared seven common exons at their 3'-ends. At their 5'-ends, the HtrA3 long form cDNA had two additional exons and the PRSS11-Like cDNA had one. Exon 1 of HtrA3 was distinct from the first exon of PRSS11-Like, possibly due to differential use of two distinct promoters initiating transcription at two different positions along the HtrA3 gene. Exon 2 of HtrA3 is identical to part of the 3'-end coding sequence of the frist exon of the PRSS11-L cDNA. FIG. 4 depicts the splice donor/acceptor sites for human HtrA3 and PRSS11-L transcripts along the HtrA3 gene. Based on these sequence alignment results, PRSS11-Like is indeed a novel alternative splice variant of the HtrA3 gene.

What is claimed is:

1. An isolated nucleic acid molecule comprising the nucleotide sequence of SEQ ID NO:1.

2. An isolated nucleic acid molecule encoding a polypeptide comprising the amino acid sequence of SEQ ID NO:2.

3. An expression vector comprising the nucleic acid molecule of claim 2.

4. A recombinant host cell containing the vector of claim 3.

* * * * *